(12) United States Patent
Pan

(10) Patent No.: US 8,597,229 B2
(45) Date of Patent: Dec. 3, 2013

(54) AUTOMATED PERITONEAL DIALYSIS CYCLER AND METHODS OF USE

(75) Inventor: Li Pan, Arcadia, CA (US)

(73) Assignee: VR Medical Technology, LLC, Clearwater, FL (US)

(*) Notice: Subject to any disclaimer, the term of this patent is extended or adjusted under 35 U.S.C. 154(b) by 111 days.

(21) Appl. No.: 12/973,673

(22) Filed: Dec. 20, 2010

(65) Prior Publication Data
US 2011/0160649 A1    Jun. 30, 2011

Related U.S. Application Data

(60) Provisional application No. 61/284,745, filed on Dec. 24, 2009.

(51) Int. Cl.
*A61M 1/00* (2006.01)
(52) U.S. Cl.
USPC ................. 604/29; 604/30; 604/500
(58) Field of Classification Search
USPC ............................. 604/29, 30, 500
See application file for complete search history.

(56) References Cited

U.S. PATENT DOCUMENTS

| | | | |
|---|---|---|---|
| 4,560,472 A | 12/1985 | Granzow et al. |
| 4,585,436 A | 4/1986 | Davis et al. |
| 4,826,482 A | 5/1989 | Kamen |
| 4,976,162 A | 12/1990 | Kamen |
| 5,004,459 A | 4/1991 | Peabody et al. |
| 5,324,422 A | 6/1994 | Colleran et al. |
| 5,338,293 A | 8/1994 | Jeppsson et al. |
| 5,350,357 A | 9/1994 | Kamen et al. |
| 5,421,823 A | 6/1995 | Kamen et al. |
| 5,431,626 A | 7/1995 | Bryant et al. |
| 5,438,510 A | 8/1995 | Brant et al. |
| 5,474,683 A | 12/1995 | Bryant et al. |
| 5,628,908 A | 5/1997 | Kamen et al. |
| 5,643,201 A | 7/1997 | Peabody et al. |
| 5,722,947 A | 3/1998 | Jeppsson et al. |
| 6,327,895 B1 | 12/2001 | Jeppsson et al. |
| 6,585,682 B1 | 7/2003 | Haraldsson et al. |
| 7,648,479 B2 | 1/2010 | Solovay et al. |
| 7,935,074 B2 | 5/2011 | Plahey et al. |
| 7,957,927 B2 | 6/2011 | Huitt et al. |
| 8,002,758 B2 | 8/2011 | Kamen et al. |
| 8,062,285 B2 | 11/2011 | Langloss et al. |
| 2004/0215129 A1 | 10/2004 | Edgson et al. |
| 2006/0195064 A1 | 8/2006 | Plahey et al. |
| 2007/0112297 A1 | 5/2007 | Plahey et al. |
| 2008/0033364 A1 | 2/2008 | Kamen et al. |
| 2008/0208111 A1 | 8/2008 | Kamen et al. |

(Continued)

OTHER PUBLICATIONS

The Portable INPERSOL CYCLER 1000, brochure from Abbott Laboratories, Renal Care, Jan. 1989, 6 pages.

(Continued)

*Primary Examiner* — Bhisma Mehta
(74) *Attorney, Agent, or Firm* — Knobbe, Martens, Olson & Bear LLP

(57) ABSTRACT

Automated peritoneal dialysis (APD) cycler systems and methods are disclosed. The APD cycler can include a heater tray with load cells configured to measure the weight of fluid contained within a heater bag and/or a drain bag. The load cells can be toggleable between enabled and disabled configurations. The APD cycler can include a pressure-based volume measurement system, which can be used to confirm measurements made by the load cells. In some embodiments, the APD cycler can have algorithms for tracking an estimated patient volume to prevent overfilling the patient.

20 Claims, 19 Drawing Sheets

(56) References Cited

U.S. PATENT DOCUMENTS

| | | |
|---|---|---|
| 2008/0253427 A1 | 10/2008 | Kamen et al. |
| 2009/0101549 A1 | 4/2009 | Kamen et al. |
| 2009/0299273 A1 | 12/2009 | Lee et al. |
| 2010/0137782 A1 | 6/2010 | Jansson et al. |
| 2010/0191180 A1 | 7/2010 | Childers et al. |
| 2010/0192686 A1 | 8/2010 | Kamen et al. |
| 2010/0234809 A1 | 9/2010 | Kenley et al. |
| 2010/0327849 A1 | 12/2010 | Kamen et al. |
| 2011/0071465 A1 | 3/2011 | Wang et al. |
| 2011/0092894 A1 | 4/2011 | McGill et al. |
| 2011/0098635 A1 | 4/2011 | Helmore et al. |

OTHER PUBLICATIONS

Snowman, "Lyophilization under Barrier Technology," Chapter 12, *Aseptic Pharmaceutical Manufacturing II: Applications for the 1990s*, pp. 311-335, Groves, et al. Editors, 1995, ISBN: 0-935184-77-5.

Lysfford, et al. "Barrier Isolation Technology: A Systems Approach," Chapter 14, *Aseptic Pharmaceutical Manufacturing II: Applications for the 1990s*, pp. 369-414, Groves, et al. Editors, 1995, ISBN: 0-935184-77-5.

International Search Report and Written Opinion issued to corresponding international application No. PCT/US2010/061378 on Jul. 18, 2011.

AUTOMATED PERITONEAL DIALYSIS CYCLER AND METHODS OF USE

CROSS-REFERENCE TO RELATED APPLICATIONS

This application claims the benefit under 35 U.S.C. §119 (e) of U.S. Provisional Patent Application No. 61/284,745, filed on Dec. 24, 2009, titled AUTOMATED PERITONEAL DIALYSIS CYCLER EMPLOYING REDUNDANT FLUID MEASUREMENT SYSTEMS, the entirety of which is hereby incorporated by reference herein and made a part of this specification for all it discloses.

INCORPORATION BY REFERENCE

The following references are hereby incorporated by reference herein in their entirety and made a part of this specification for all that they disclose: U.S. Patent Publication No. 2006/0195064; U.S. Patent Publication No. 2007/0112297; U.S. Pat. Nos. 4,560,470; 4,585,436; 4,826,482; 4,976,162; 5,421,823; 5,324,422; 5,338,293; 5,350,357; 5,421,823; 5,474,683; 5,722,947; and chapters 12 and 14 of Aseptic Pharmaceutical Manufacturing II (ISBN: 0-935184-77-5). The devices, structures, compositions, methods, and procedures disclosed in these references are provided as background and can be used in addition to or instead of those disclosed in various sections of this application.

BACKGROUND OF THE DISCLOSURE

1. Field of the Disclosure

The present disclosure relates generally to systems and method for conducting dialysis treatment, and more specifically to systems and methods for conducting automated peritoneal dialysis treatment.

2. Background

Although systems and methods for conducting dialysis treatment exist, there remains a need for improved automated peritoneal dialysis systems and methods.

SUMMARY OF THE INVENTION

Some example embodiments are summarized below. In some embodiments, a dialysis system can have a pressure-based volume measurement system. The dialysis system can include a containment chamber and a reference chamber, and one or more pumps configured to control the pressure within the containment chamber and reference chamber. The dialysis system can have a controller configured to set the containment chamber to a first pressure and to set the reference chamber to a second pressure. The controller can open a connection between the containment chamber and reference chamber so that the pressures are allowed to substantially equalize. The equalized pressure can then be measured in one or both of the containment chamber and the reference chamber.

One or both of the first and second pressures can be a negative pressure. In some embodiments, the second pressure in the containment chamber can be a higher negative pressure than the first pressure in the containment chamber. In some embodiments, the ratio between the pressure of the reference chamber and the pressure of the containment chamber can be greater than about 2 to 1, 4 to 1, or 10 to 1. In some embodiments, positive pressures may be used in one or both of the containment chamber and reference chamber. The reference chamber can have a higher pressure therein than does the containment chamber. In some embodiments, the first pressure applied to the containment chamber is a negative pressure at least about −0.1 psig and/or of less than or equal to −1.0 psig or −0.5 psig. In some embodiments, a negative pressure of at least about −5.0 psig and/or less than or equal to about −9.0 psig. In some embodiments, the containment chamber or the reference chamber can be set to substantially atmospheric pressure.

The controller can be configured to calculate the volume of gas inside the containment chamber based at least in part on the measured equalized pressure. The controller can be configured to determine a volume of an amount of fluid in at least one of a heater bag and a drain bag based at least in part on the calculated volume of gas inside the containment chamber.

One or more pressure sensors can be configured to measure the pressure in the containment chamber and the reference chamber. The system can also include temperature sensors in some embodiments, and the controller can be configured to determine the volume of gas inside the containment chamber at least in part on a measured change in temperature in one or both of the containment chamber and the reference chamber.

The system can have a weigh scale configured to measure the weight of an amount of fluid in at least one of a heater bag and a drain bag. The pressure-based volume measurement system can be used to confirm measurements made using the weigh scale (which can include, for example, one or more load cells). The controller can be configured to compare the measurement of the weigh scale to the calculated volume of the amount of fluid in at least one of the heater bag and the drain bag, and the controller can post an alarm if the calculated volume differs from the measurement of the weigh scale by more than a threshold amount. The controller can use the weight measured by the weigh scale to determine a volume of fluid and compare that volume with the volume measured by the pressure-based volume.

The volume of the containment chamber can be determined by applying a first pressure to the containment chamber using one or more pumps, applying a second pressure to the reference chamber using the one or more pumps, opening a pathway between the containment chamber and the reference chamber, allowing the pressures of the containment chamber and the reference chamber to substantially equalize, measuring an equalized pressure in at least one of the containment chamber and the reference chamber, and calculating, using one or more computing devices, the first volume of gas inside the containment chamber based at least in part on the measured equalized pressure.

A volume of an amount of fluid in at least one of the heater bag and the drain bag can be determined based at least in part on the calculated first volume of gas inside the containment chamber.

The weight of an amount of fluid in at least one of the heater bag and the drain bag can be measured using a weigh scale, and that weight can be compared to the calculated volume of the amount of fluid in at least one of the heater bag and the drain bag. An alarm can be posted an alarm if the calculated volume differs from the measurement of the weigh scale by more than a threshold amount. The weight can be used to calculate a volume of fluid to be compared to the volume of fluid that was calculated from the equalized pressure.

A load cell can be used to measure the weight applied to a tray of a dialysis system. The load cell can be toggleable between an enabled configuration and a disabled configuration. When the system is moved, or not in use, the load cell can be set to the disabled configuration so that movement, or vibrations, etc. do not damage the load cell. The load cell can include a main body and a sensor configured to generate a signal representative of force applied to the main body. A tray can be coupled to the main body. An isolation member (such as a screw) can be moveable between an enabled position and a disabled position. When the isolation member is in the enabled position, weight applied to the tray is transferred to the main body to generate a signal using the sensor that is representative of the weight applied to the tray. When the isolation member is in the disabled position, the weight applied to the tray is transferred through the isolation member such that the weight is not applied to the main body.

The load cell can have a support bar, and the isolation member can be configured to engage the support bar when in the disabled position such that the weight from the tray is transferred through the isolation member to the support bar.

The system can have multiple load cells that can be configured to operate in parallel such that the measurements of the plurality of load cells are combined to produce a value representative of the weight applied to the tray.

In some embodiments, the dialysis system can be configured to reduce the pressure applied when draining fluid (e.g., from a patient) when the drain nears completion. A dialysis system can have a sealed containment chamber, a drain container positioned inside the containment chamber, and a patient line in fluid communication with the drain container. The patient line can configured to attach to a patient catheter. A controller can be configured to apply a negative pressure to the containment chamber, using one of more pumps, such that fluid is drawn through the patient line into the drain container. The flow rate can be monitored, and the controller can reduce the negative pressure in the containment chamber in response to a measured reduction in the flow rate of fluid into the drain container.

The controller can be configured to gradually reduce the negative pressure in the containment chamber as the flow rate of fluid into the drain bag reduces. The controller can be configured to maintain the negative pressure in the containment chamber at a substantially constant level until the flow rate drops below a first threshold rate, and the controller can be configured to reduce the negative pressure in response to the flow rate dropping below the first threshold level. The controller can be configured to stop the drain of fluid into the drain bag in response to the flow rate dropping below a second threshold level.

In some embodiments, the system can be configured to track an estimated patient volume (e.g., the amount of fluid present in the patient peritoneum), to prevent overfilling. The system can infuse an infusion volume of dialysis solution into a patient. The system can drain fluid from a patient, identify an indicator that the drain is complete, and measure the volume of fluid in the drain bag. The system can calculate a minimum drain volume as a predetermined percentage of the expected drain volume. The expected drain volume can be the infusion volume from the previous fill stage plus an estimated residual patient volume. In some cases, the expected drain volume can also include an expected ultrafiltration volume. The system can determine, using one or more computing devices, if the measured volume of fluid is less than the minimum drain volume.

The system can post an alarm if the measured volume of fluid is less than the minimum drain volume. The system can continue the dialysis treatment if the measured volume of fluid is not less than the minimum drain volume. The system can update the estimated residual patient volume to be the difference between the expected drain volume and the measured volume. The system can perform a subsequent infusion stage and a subsequent drain stage, and the system can use the updated estimated residual patient volume to calculate the minimum drain volume for the subsequent drain stage.

A connector can allow for a sealed container (e.g., a bag) to be opened without introducing contamination. The connector can include a port configured to attach to a container for containing fluid, the port having a septum configured to seal the container, a tube connector configured to attach to a tubing element, and a spike attached to the tube connector. The spike can pierce the septum of the bag port when the tube connector is advanced toward the port such that a fluid connection if formed from the container through the port, through a fluid pathway in the spike, through the tube connector, and into the tube element. A seal member can be attached at a first end to the port and attached at a second end to the tube connector. The seal member can provide a seal between the bag port and the tube connector such that the spike can be advanced to pierce the septum without exposing the spike or septum to the outside environment.

The seal member can be a bellows member. One or more guide members can be configured to guide the spike toward the septum as the spike is advanced.

In some embodiments, one or more protective cover pieces can be included and can be configured to maintain the tube connector at distance from the port at which the spike does not pierce the septum. The one or more protective cover pieces can be removable to allow the spike to be advanced to pierce the septum.

BRIEF DESCRIPTION OF THE DRAWINGS

Certain embodiments of the inventions will now be discussed in detail with reference to the following figures. These figures are provided for illustrative purposes only, and the inventions are not limited to the subject matter illustrated in the figures.

DETAILED DESCRIPTION OF EXAMPLE EMBODIMENTS

Figure 1:
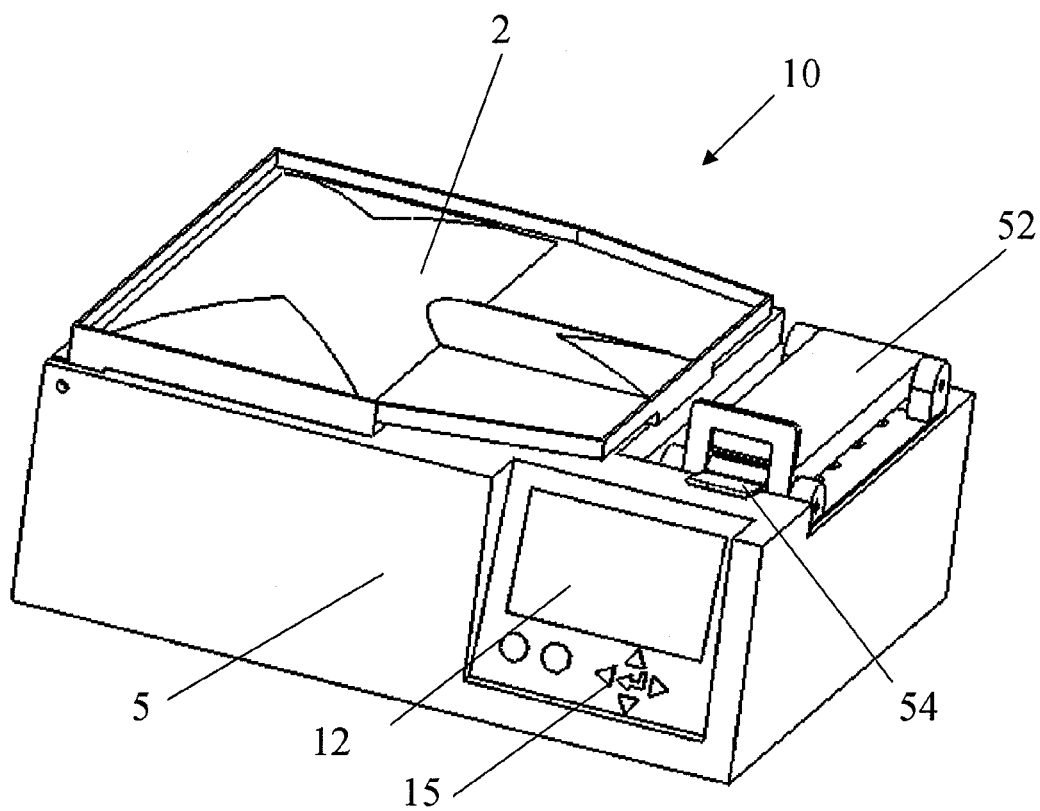
FIG. 1 is a perspective view of an example embodiment of an APD cycler.

The following detailed description is now directed to certain specific embodiments of the disclosure. In this description, reference is made to the drawings wherein like parts are designated with like reference numerals throughout the description and the drawings.

FIG. 1 is a perspective view of an example embodiment of an Automated Peritoneal Dialysis (APD) system 10, often referred to herein as an APD cycler 10. The APD cycler 10 can include a housing 5. A cover 2, such as a heater/weigh scale cover, can be attached to the housing 5 (e.g., using one or more hinges) so that the heater/weigh scale cover 2 can open and close like a door. In FIG. 1, the heater/weigh scale cover 2 is shown in the closed position. An access region, such as pinch valve access door 52, can be attached to the housing 5 (e.g., using one or more hinges) so that the pinch valve access door 52 can open and close. The pinch valve access door 52 is shown in the closed configuration in FIG. 1. A closure, such as latch 54, can be used to maintain the pinch valve access door 52 in the closed position. A closure, such as a latch (not shown in FIG. 1), can also be used to maintain the heater/weigh scale cover 2 in the closed position. The heater/weigh scale cover 2 and/or the pinch valve access door 52 can be maintained closed using closures such as pins, or a snap or friction fit structure, or in any other suitable manner.

The APD cycler 10 can include a user output, such as display 12, and a user input, such as control buttons 15, which can be recessed and/or fully contained within the profile of the housing 5, to prevent the display 12 and buttons 15 from being damaged, for example, during movement of the APD cycler 10. The display 12 can be configured to provide information to the user and to request information from the user, as described herein. The buttons 15 can be configured to receive user input as described herein. In some embodiments, the display 12 can be a touch screen, thereby reducing the number of buttons 15, or allowing for the buttons 15 to be omitted.

Figure 2:
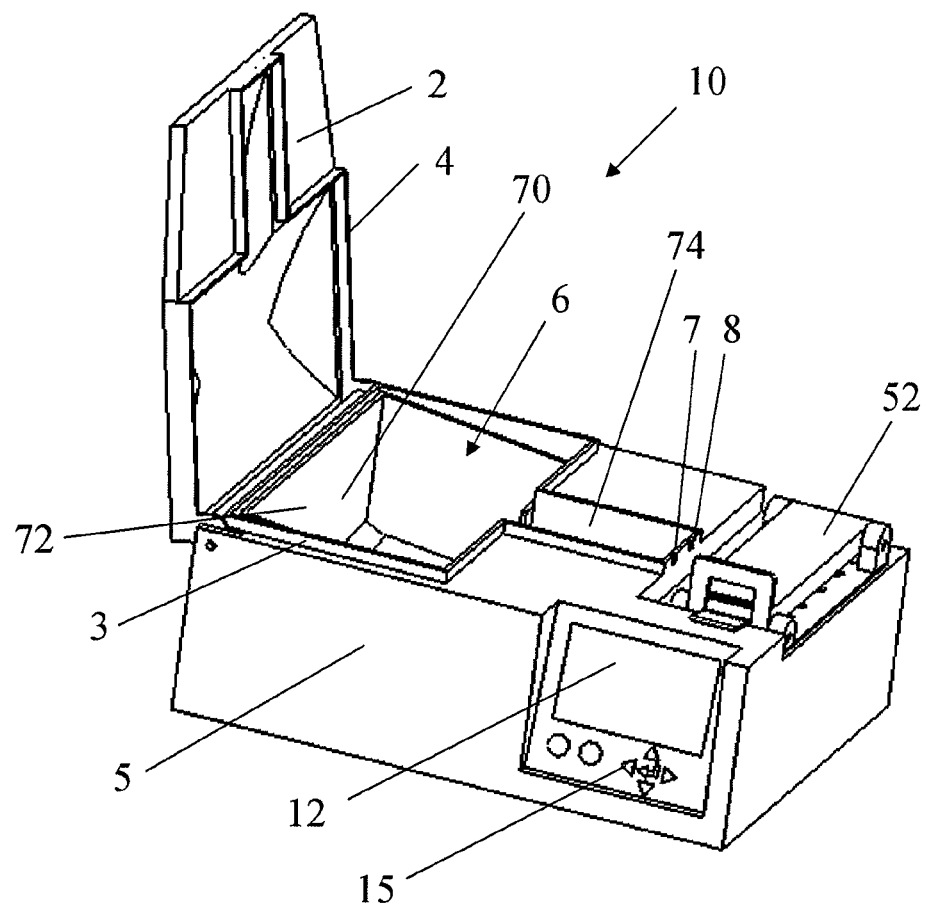
FIG. 2 is another perspective view of the APD Cycler of FIG. 1 with the heater/weigh scale cover in an open position.
Figure 5:
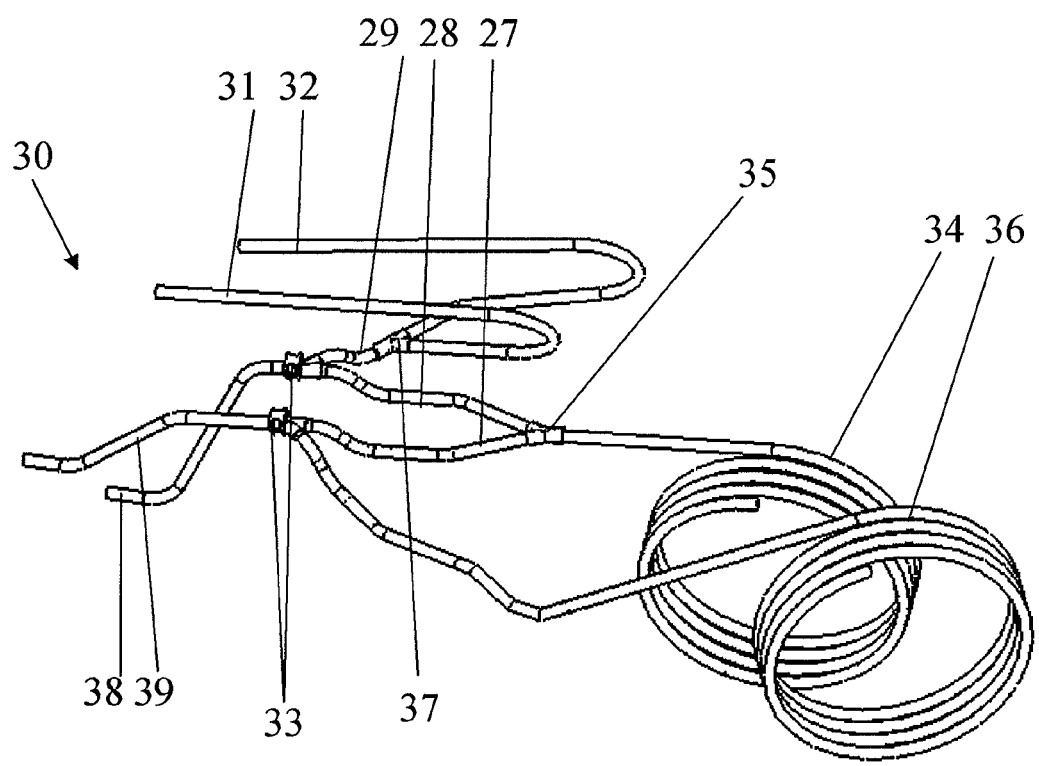
FIG. 5 is a perspective view of an example embodiment of a disposable set for use with the APD cycler with no heater bag or drain bag attached thereto.

FIG. 2 is a perspective view of the APD cycler 10 with the heater/weigh scale cover 2 in the open position. A heater tray assembly 70 can be positioned in a recess formed in the housing 5 so that it is protected from unintentional forces that can cause errors in weight measurements taken using the heater tray 72. In some embodiments, the heater tray assembly 70 can be removable from the recess, for example to provide access to components of the weigh scale. The heater tray assembly 70 can be substantially enclosed on the bottom and sides by walls 71 and the top of the heater tray assembly 70 can be open so that components of a disposable set 30 can be placed therein, as shown in FIG. 5. The housing 5 can include a housing lip 3 that extends up to receive a cover lip 4 formed on the underside of heater/weigh scale cover 2. The cover lip 4 can mate with the housing lip 3 to form a containment chamber 6 therebetween, and these components can be configured to form a seal, for example, so that negative pressure can be maintained inside the containment chamber 6, as described herein. The housing 5 can have a channel 74 leading away from the heater tray assembly 70, and the housing lip 3 can extend substantially around the channel 74. Grooves 7 and 8 can be formed in the housing lip 3. Many alternatives are possible. For example, the heater/weigh scale cover 2 can be configured to seal directly with the walls 71 of the heater tray assembly 70.

Figure 3:
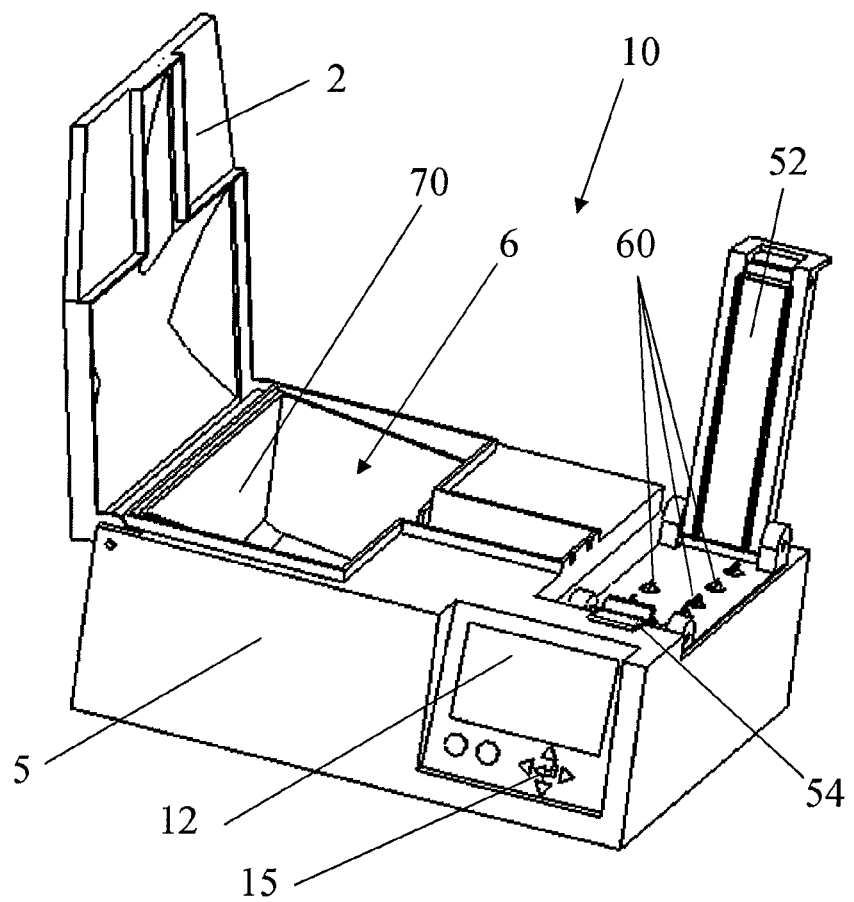
FIG. 3 is another perspective view of the APD Cycler of FIG. 1 with the pinch valve access door in an open position.

FIG. 3 is a perspective view of the APD cycler with the pinch valve access door 52 in the open position. For example, the user can disengage the latch 54 to open the pinch valve access door 52, thereby exposing the pinch valve actuators 60. In the embodiment shown in FIG. 3, the APD cycler 10 can be configured to receive a disposable set 30.

Figure 4:
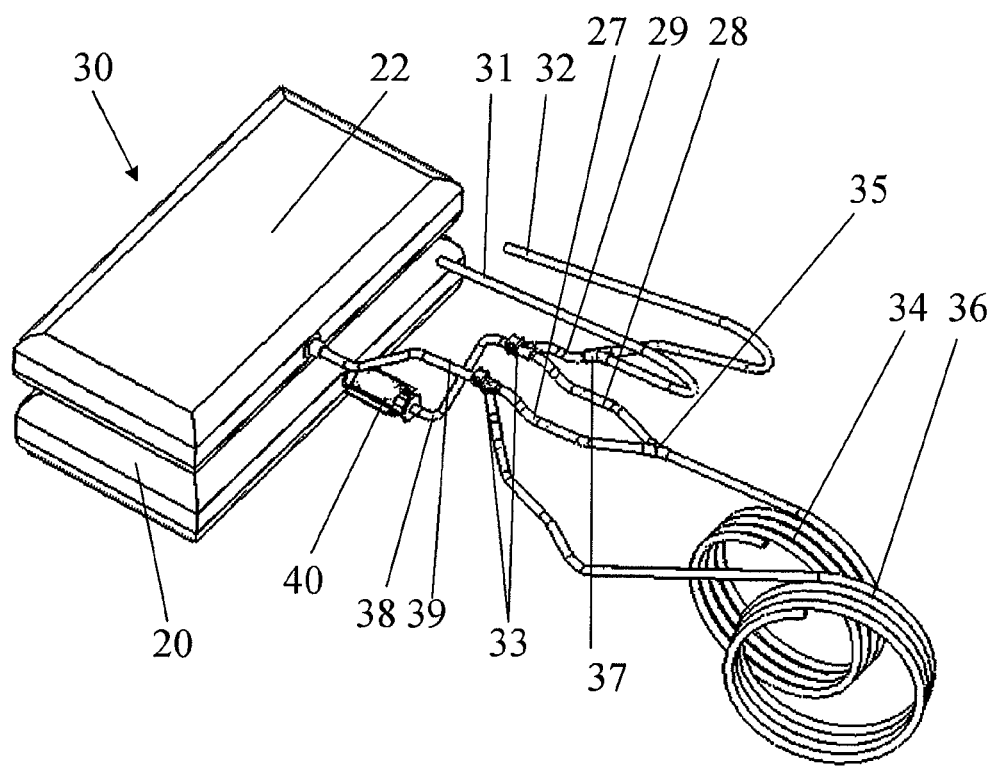
FIG. 4 is a perspective view of an example embodiment of a disposable set for use with the APD cycler of FIG. 1.

FIG. 4 is a perspective view of an example embodiment of a disposable set 30 that includes an fill container, such as a heater bag 20, and a drain container, such as a drain bag 22. The heater bag 20 can be filled with fluid to be warmed before being introduce to the patient, and the drain bag 22 can be used to receive fluids drained from the patient. The disposable set 30 can include multiple supply lines 31 and 32 for introducing fluid into the heater bag, although in some embodiments a single supply line can be used. A patient line 34 can direct fluid from the heater bag 20 to the patient, and then from the patient to the drain bag 22. A drain line 36 can be used to remove fluid from the drain bag 22. Branch connections, such as Y connections 33, 35 and 37, and tubing elements 28, 29, 38, and 39 can be positioned as shown in FIG. 4 to connect the components of the disposable 30 to each other to provide a suitable flow path for fluid through the system. In some embodiments, all or portions of the tubing elements 27, 28, 29, 38, and 39 and/or portions of the supply lines 31 and 32, patient line 34, and drain line 36 can be flexible such that the pinch valve actuators 60 can pinch the tubing elements 27, 28, 29, 38, 39 to close off fluid passageways to direct the flow of fluid through the system, as described herein. Connectors (not shown) can be included on the ends of the supply line lines 31 and 32, on the end of patient line 34, and/or on the end of the drain line 36. Various suitable connectors can be used to connect these lines to a fluid source, patient catheter, or waste receptacle as appropriate. A sterile connector 40 can be used to provide access to the heater bag 20, as shown in greater detail in FIGS. 6A to 6D.

A low recirculation volume set can be created by providing long tubing lines 28 and 29 (e.g., in some cases at least about 25 cm or 50 cm or more in length) thereby moving Y connection 35 close to the patient connector on patient line 34. Fresh dialysis solution flows down line 28 and spent dialysis and ultrafiltration are fluids drained through line 29. Line 34, wherein both fresh dialysis solution and spent dialysis fluids flow, can be shortened (e.g., to less than or equal to about 10 cm, 5 cm, 1 cm, or less) so that the recirculation volume would be low or generally negligible. (Note: A 4 mm ID tube contains 1 ml of fluid for each 8 cm of length.) In some embodiments, lines 28 and 29 could remain as they are shown and patient line 34 be replaced by a double D extrusion that terminates at the patient connection limiting the recirculation volume to the volume within the catheter itself.

FIG. 5 is a perspective view of an example embodiment of a disposable set 30 that does not include the heater bag 20 or the drain bag 22. In some embodiments, the heater bag 20 and/or the drain bag 22 can be reusable, while the tubing and other components shown in FIG. 5 can be disposable. In some embodiments, the entire heater bag 20 and/or the drain bag 22 can be disposable as well. The disposable set 30 can be a low cost unit. In some embodiments, the disposable set 30 can include multiple (e.g., four) Y connections 33, 35, and 37; multiple (e.g., nine) lengths of tubing; and multiple (e.g., six) connectors, which can have tip protectors. Many alternatives are possible. For example a 4-way connection can be used instead of a Y connection, thereby reducing the number of connections and lengths of tubing (e.g., one less connection and one less length of tubing than shown in FIG. 5).

FIGS. 6a-e illustrate an example embodiment of the connector 40 that is configured to provide a fluid connection between the heater bag 20 and the tubing 38. In some embodiments, the connector 40 can be attached to the heater bag 20 and/or to the tube 38 when the disposable set is manufactured.

Figure 6A:
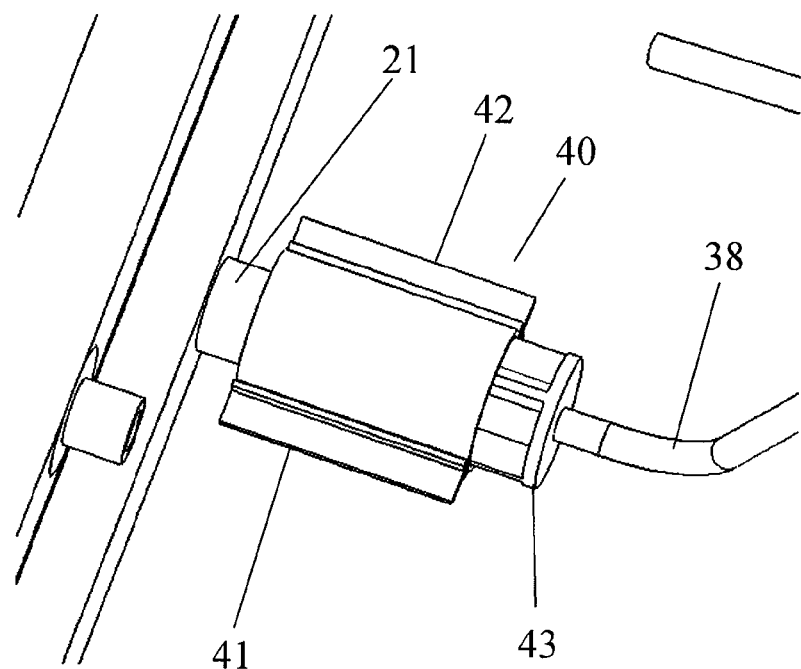
FIGS. 6A-E illustrate an example embodiment of a connector for attaching the heater bag to a tubing element.
Figure 6B:
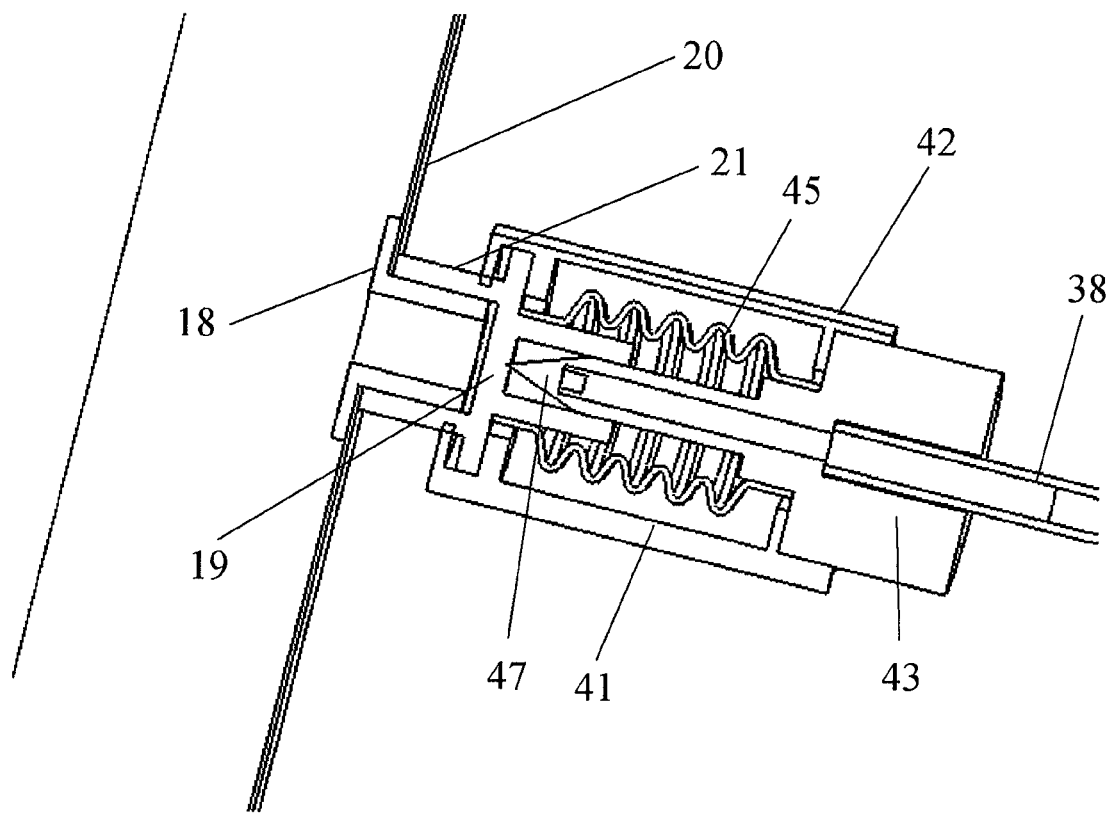

FIG. 6a is a perspective view of the connector 40 with protective covers 41 and 42 in place. A heater bag port 21 can be attached to the heater bag 20 and a tube connector 43 can be attached to the tubing 38. When engaged, the protective covers 41 and 42 can substantially secure and constrain the tube connector 43 from moving relative to heater bag port 21. FIG. 6b is a cross sectional view of the connector 40 with the protective covers 41, 42 engaged. The protective covers 41, 42 can include tabs that abut against the heater bag port 21 and against the tube connector 43 to prevent them from being advance towards each other. A port adapter 18 can be bonded to the inside surface of heater bag 20 using heat welding, ultrasonic welding, RF welding, solvent welding, adhesive welding, or other suitable manner. Adapter port 18 can be bonded to the inside surface of the heater bag 20 rather than the outside surface of the heater bag 20 to reduce the likelihood that the adapter port may be dislodged during shipping and handling. The heater bag port piece 21 can be bonded to the adapter port 18 using an adhesive or other suitable manner. In some embodiments, the heater bag adapter 21 and the adapter port 18 can be integrally formed as a single piece. The heater bag port 21 can have a septum 19 that prevents fluid from transferring between the heater bag 20 and the tube 38.

Figure 6C:
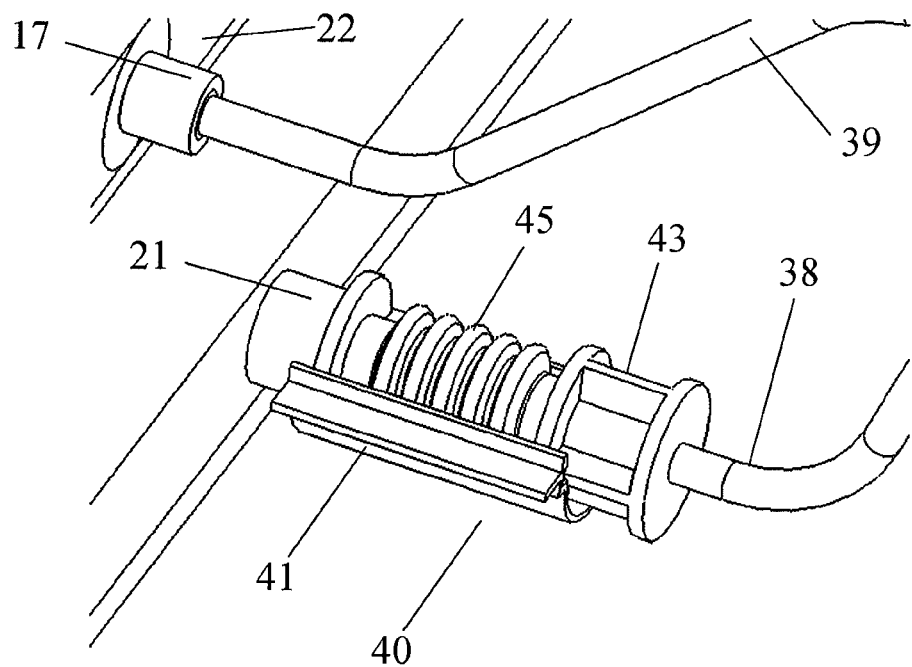
Figure 6D:
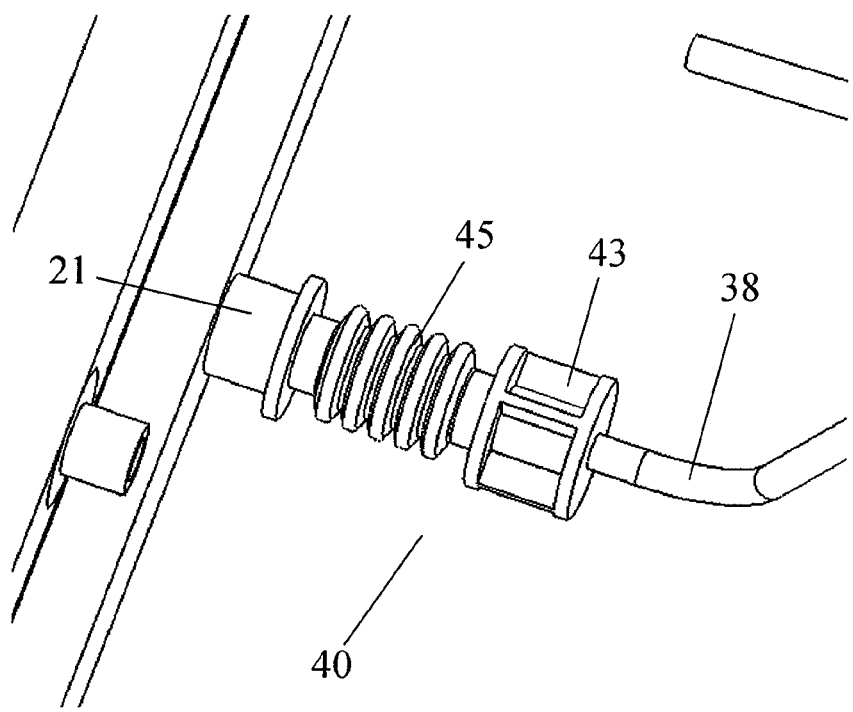
Figure 6E:
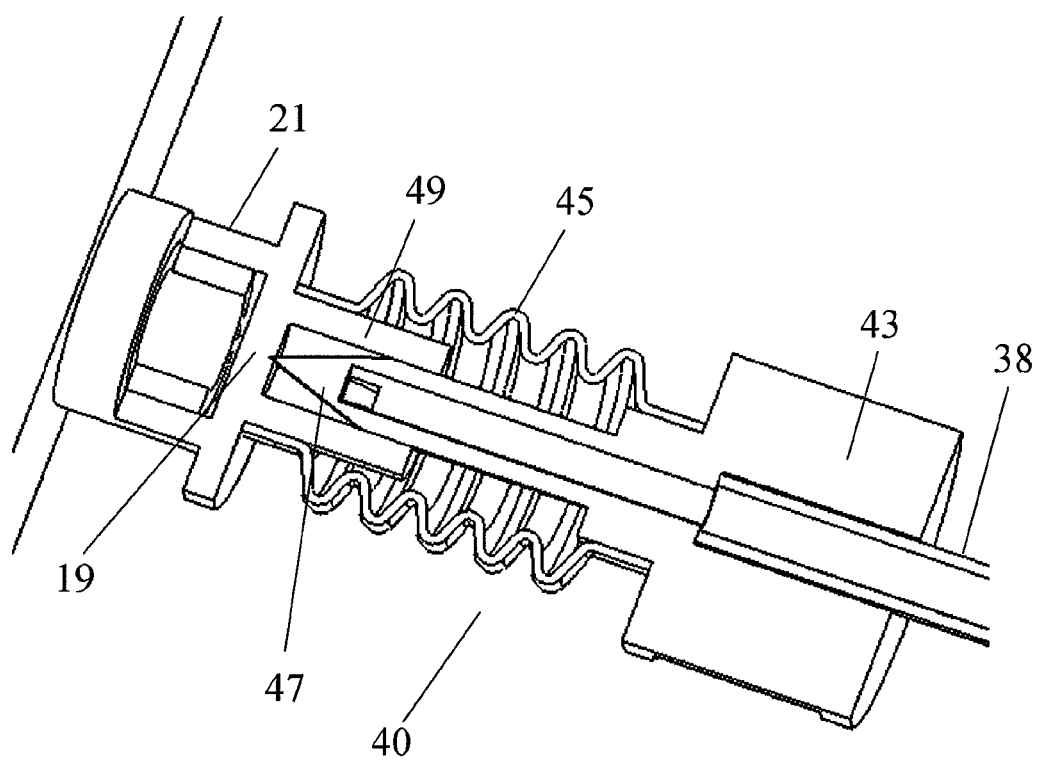

FIG. 6c shows the connector 40 with the protective cover 42 removed, exposing the flexible bellows member 45 that connects the heater bag port 21 to the tube connector 43. The bellows member 45 can be bonded on a first end to the heater bag port 21 and on a second end to the tube connector 43, using an adhesive or any other suitable manner. FIG. 6d shows connector 40 with both protective covers 41 and 42 removed. FIG. 6e is a cross sectional view of the connector 40 with the protective covers 41 and 42 removed. With the protective covers 41 and 42 removed, the tube connector 43 can be pushed towards the heater bag port 21, thereby collapsing the bellows member 45. The bellows member 45 can be made from a flexible, elastomeric, and/or resilient material, such as silicone. The tube connector 43 can have a spike 47 connected thereto. As the tube connector 43 moves toward bag port 21, the spike 47 can penetrate the septum 19, thereby aseptically initiating a fluid connection between the tube 38 and the interior of the heater bag 20. In some embodiments, the tube connector 43 and spike 47 can retract after the septum 19 is penetrated, but a fluid connection can continue to exist between the heater bag 20 and the tube 38 because fluid may pass through the hole in the pieced septum 19 formed by the spike 47. In some embodiments, the tube connector 43 and spike 47 can be retained in the advanced position (not shown) with the tip of the spike 47 protruding through the septum 19, thereby allowing fluid to flow through the septum 19 via the fluid pathway formed on the inside of the spike 47. The heater bag port 21 can include guide walls 49 that generally surround the tip of the spike 47, and the guide walls 49 can direct the spike 47 through the septum 19 to reduce the risk that the spike 47 would unintentionally puncture the bellows member 45 or another wall in the heater bag 20, or that the heater bag port 21 would dislodge, thereby generating a fluid leak.

Thus, the connector 40 can provide a barrier that seals off the interior of the heater bag 20 until the spike 47 is advanced to puncture the septum 19, for example when the user is ready to begin a dialysis procedure. In some embodiments, the heater bag 20 can be prefilled with a fluid for delivery to a patient, and the septum 19 can provide a barrier to maintain that fluid inside the heater bag 20 until the septum 19 is punctured. The connector can also prevent bacteria or other contaminants from entering the heater bag 20 or other components of the disposable set 30. The connector 40 can allow for the seal to the heater bag 20 to be broken without introducing any bacteria or other contaminants, thereby maintaining the sterile environment inside the disposable set 30. For example, the user can advance the spike 47 to pierce the septum 19 without touching the spike 47, and the bellows member 45 can function to seal off the inside of the connector 40 in both the advanced and retracted positioned discussed above. The connector 40 can be designed so that it is permanently connected to the heater bag 20 and tube 38 and not designed to be disconnection therefrom during normal use. For example, the bellows member 45 can be adhered to the heater bag port 21 and to the tube connector 43, which can be adhered to the heater bag 20 and the tube 38, respectively. Thus, in some embodiments, the connector 40 does not allow for disconnection of the tube 38 from the heater bag 20. Rather, the connector 40 remains connected thereto during use, and can be transitioned from a closed state to an open state by advancing the spike 47 through the septum 19 without opening the connector 40 or otherwise exposing the interior of the connector 40 to the surrounding environment. Also, the connector 40 can be configured to remain open after it has been initially opened (e.g., advanced to pierce the septum 19), and not reseal or close if the connector is later set to the retracted position. Thus, the connector 40 may be designed to not be capable of repeated transitions between open and closed configurations.

Various alternative connectors can be used to connect the tube 38 to the heater bag 20. For example, in some embodiments, the heater bag 20 can have a male or female luer connector attached thereto and can be configured to selectively attach to a corresponding male or female luer attached to the tube 38. This embodiment may be advantageous if the heater bag is intended to be reused and if the tubing is intended to be disposable, because the male luer can be disengaged from the female luer to allow the heater bag to be disconnected from the tube 38. In some embodiments, the tube 38 can be connected directly to the adapter port 18 of the heater bag 20 with no septum or other barrier to seal the heater bag 20. This configuration can be used, for example, if the heater bag is not prefilled, so that it is inserted empty into the ADP cycler 10 and is thereafter filled with fluid via the supply lines 31, 32. In some cases, user can mix two or more fluids (e.g., having different dextrose concentrations) to form a mixture (e.g., having an intermittent dextrose concentration), which can allow for better ultrafiltration control. A prefilled heater bag can be used, thereby reducing the cost of the therapy. In some embodiments, the supply lines 31 and 32 can be omitted, for example, if the prefilled heater bag is sufficiently large to contain the full volume of treatment fluid (e.g., for pediatric or small-mass patient use, or using a large volume heater bag.)

With reference now to FIG. 6c, the tube 39 can be directly connected to an adapter port 17, which can be bonded to the inside of the drain bag 22 in a manner similar to that described in connection with the adapter port 18 above. Thus, in some embodiments, no septum or other barrier is provided between the tube 39 and the drain bag 22. In some embodiments, a connector similar to the connector 40 can be used to seal the drain bag 22 until the use. Also, detachable connectors (e.g., male and female luer connectors) can be used so that the drain bag 22 is removable from the tube 39.

The disposable set 30 can be sterilized. For example, the heater bag 20 can be prefilled and then steam sterilized. The prefilled heater bag 20 can be referred to as the wet side of the disposable set 30. The dry side of the disposable set 30 can include the lines 31, 32, 34, 36; tubing 27, 28, 29, 38, 39; multi-line connections, such as Y connections 33, 35, 37; empty drain bag 22; and end connections (not shown). The dry side of the disposable set 30 can be assembled and sterilized, such as by using ethylene oxide gas, Gamma radiation, or Electron Beam sterilization. The wet side and the dry side of the disposable set 30 can exit their respective sterilizers in a sterile barrier "isolation" environment and can be aseptically joined by the connector 40. Some suitable sterile barrier "isolation" environments, and other details relating to the sterilization are described in chapters 12 and 14 of Aseptic Pharmaceutical Manufacturing II (ISBN: 0-935184-77-5). Many alternatives are possible. For example, the wet side and dry side of the disposable set 30 can be joined in a clean room environment while an Electron Beam sterilizes the connection. In embodiments in which the heater bag 20 is not prefilled, the entire disposable set 30 can be assembled as the dry side and can be sterilized after assembly using any of the suitable sterilization techniques described herein.

In some embodiments, the bags 20 and 22 can have ports located on the side. The side port location can allow the cycler to be designed such that its overall dimensions are compact (e.g., to better fit into an airplane overhead storage bin).

Figure 7:
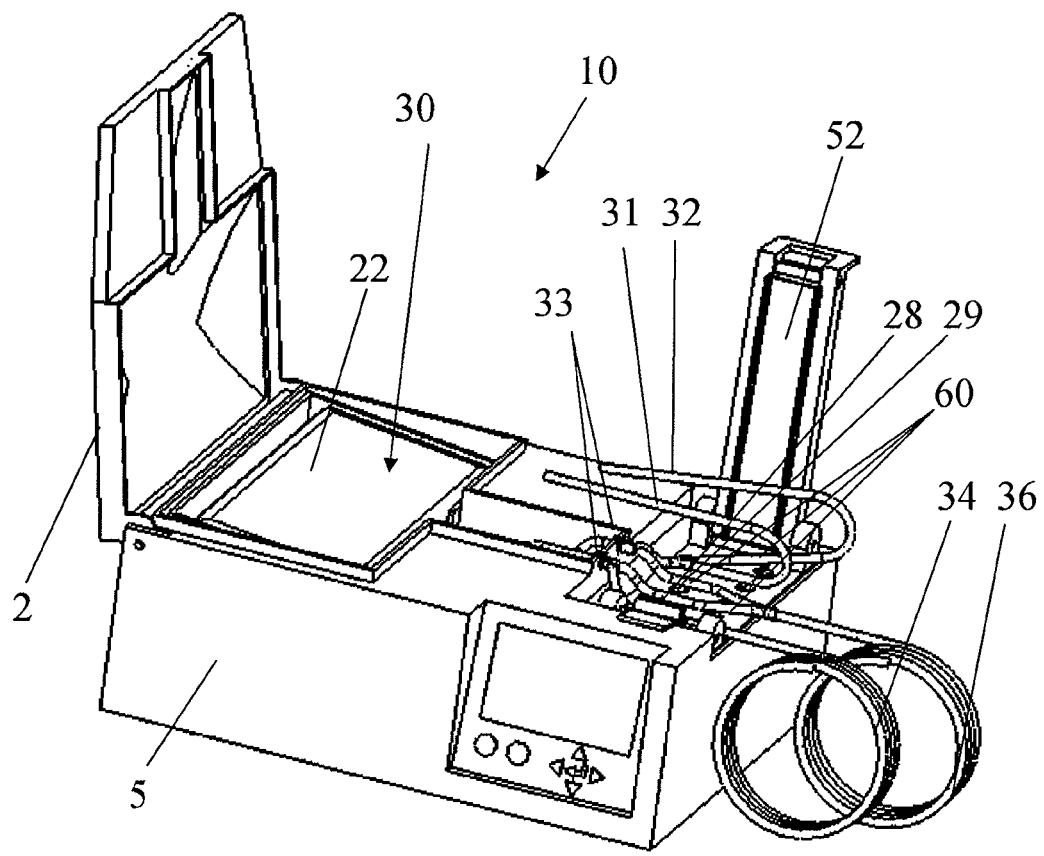
FIG. 7 is another perspective view of the APD Cycler of FIG. 1 with the disposable set of FIG. 4 loaded therein.

FIG. 7 is a perspective view of the APD cycler 10 with the disposable set 30 positioned therein. The heater bag 20 can be positioned, for example, at the bottom of the heater tray assembly, near one or more heating elements (not shown) such that fluid introduce into the heater bag 20 can be warmed before delivery to the patient. The drain bag 22 can also be placed into the containment chamber 6 along with the heater bag 20, as shown. The Y connections 33 can fit into the grooves 7 and 8, and can be configured to form a substantially vacuum tight seal when the heater/weigh scale cover 2 is closed. For example, the Y connections 33 can include O-rings that are sized larger than the grooves 7 and 8 such that the O-rings are compressed when inserted into the grooves 7 and 8 to form the seal. The connector 40 and portions of the tubing elements 38 and 39 can be positioned in the channel 74. The disposable set 30 can be positioned such that pinch valves 60 are located directly beneath flexible portions of the tubing such that the pinch valves 60 can resiliently deform portions of the tubing to prevent the flow of fluid therethrough, to thereby direct the flow of fluid through the system. The APD cycler 10 can be configured to hold the flexible pieces of tubing in position over the corresponding pinch valves 60 during use. In some embodiments, the underside of the pinch valve access door 52 can have grooves or slots (not shown) configured to receive the tubing therein to position the pieces of tubing above the pinch valves 60 when the pinch valve access door 52 is closed. A series of clamps (not shown) can be included to position the pieces of tubing above the corresponding pinch valves 60.

Figure 8:
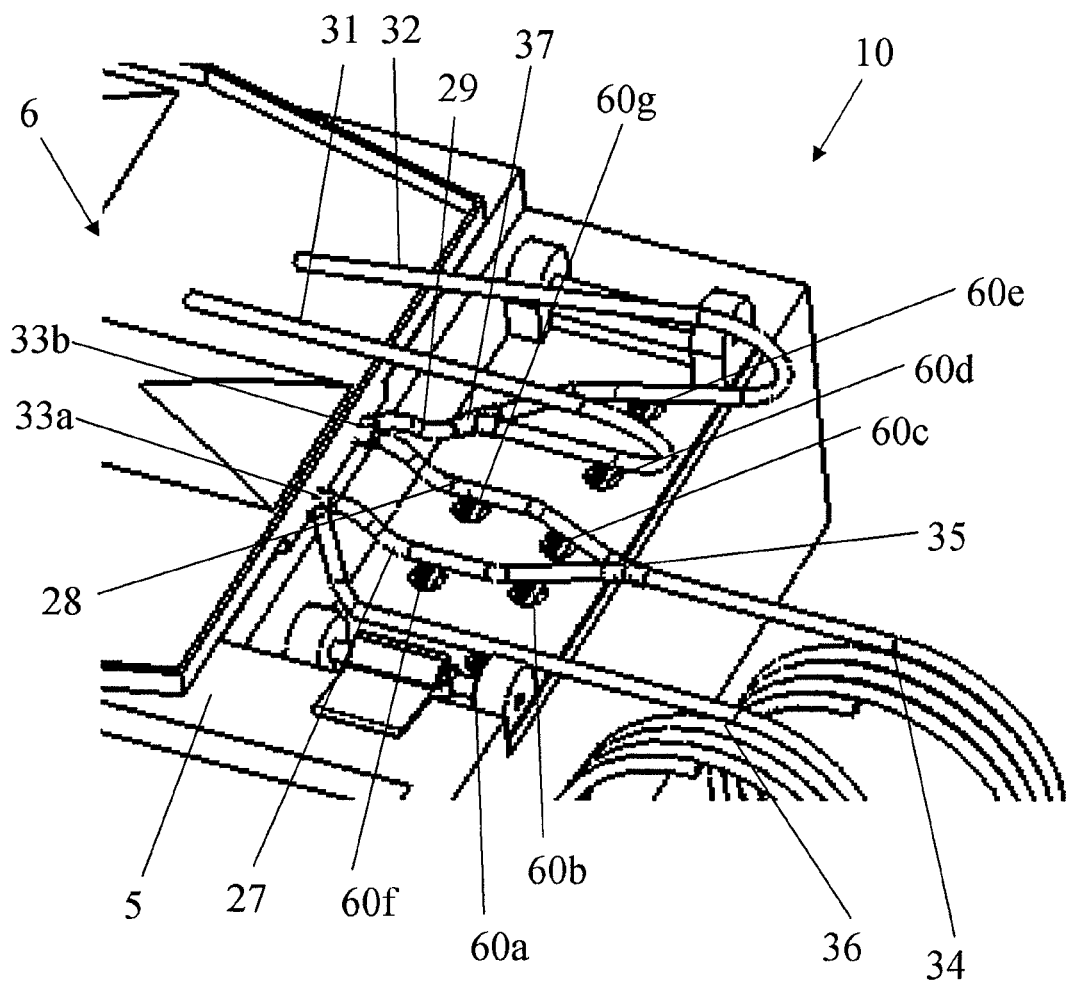
FIG. 8 is a close-up perspective view of the APD Cycler of FIG. 1 with the pinch valve access door removed to show the tubing elements aligned with the corresponding pinch valves.

FIG. 8 is a partial perspective view of the APD cycler 10 with the pinch valve access door 52 omitted from view. The supply lines 31 and 32 are positioned above the pinch valves 60$d$ and 60$e$, respectively, such that the pinch valves 60$d$ and 60$e$ can control the flow of fluid through the supply lines 31 and 32, such as when a fresh volume of fluid is transferred into the heater bag 20. The tubing element 28 that interconnects the patient line 34 to the heater bag 20 can be positioned above the pinch valves 60$c$ and 60$g$ such that the pinch valves 60$c$ and 60$g$ can control the flow of fluid through the tubing element 28, such as when the fresh, heated fluid is transferred from the heating bag 20 to the patient line 34 for delivery to the patient. The tubing element 27 that interconnects the patient line 34 to the drain bag 22 is positioned above the pinch valves 60$b$ and 60$f$ such that the pinch valves 60$b$ and 60$f$ can control the flow of fluid through the tubing element 27, such as when fluid is drained from the patient via the patient line 34 to the drain bag 22. The drain line 36 can be positioned over pinch valve 60$a$ such that the pinch valve 60$a$ can control the flow of fluid through the drain line 36, such as when fluid that was drained from the patient is transported from the drain bag 22 out via the drain line 36. In the illustrated embodiment, the tubing elements 27 and 28 that connect to the patient line 34 can have multiple (e.g., two) pinch valves 60$b$ and 60$f$ or 60$c$ and 60$g$ associated therewith, so that if one pinch (e.g., 60$c$) valve fails or malfunctions, another pinch valve (e.g., 60$g$) can still close the tubing, thereby reducing the likelihood that a valve malfunction would adversely affect the patient (e.g., overfilling or excess drainage).

Figure 9:
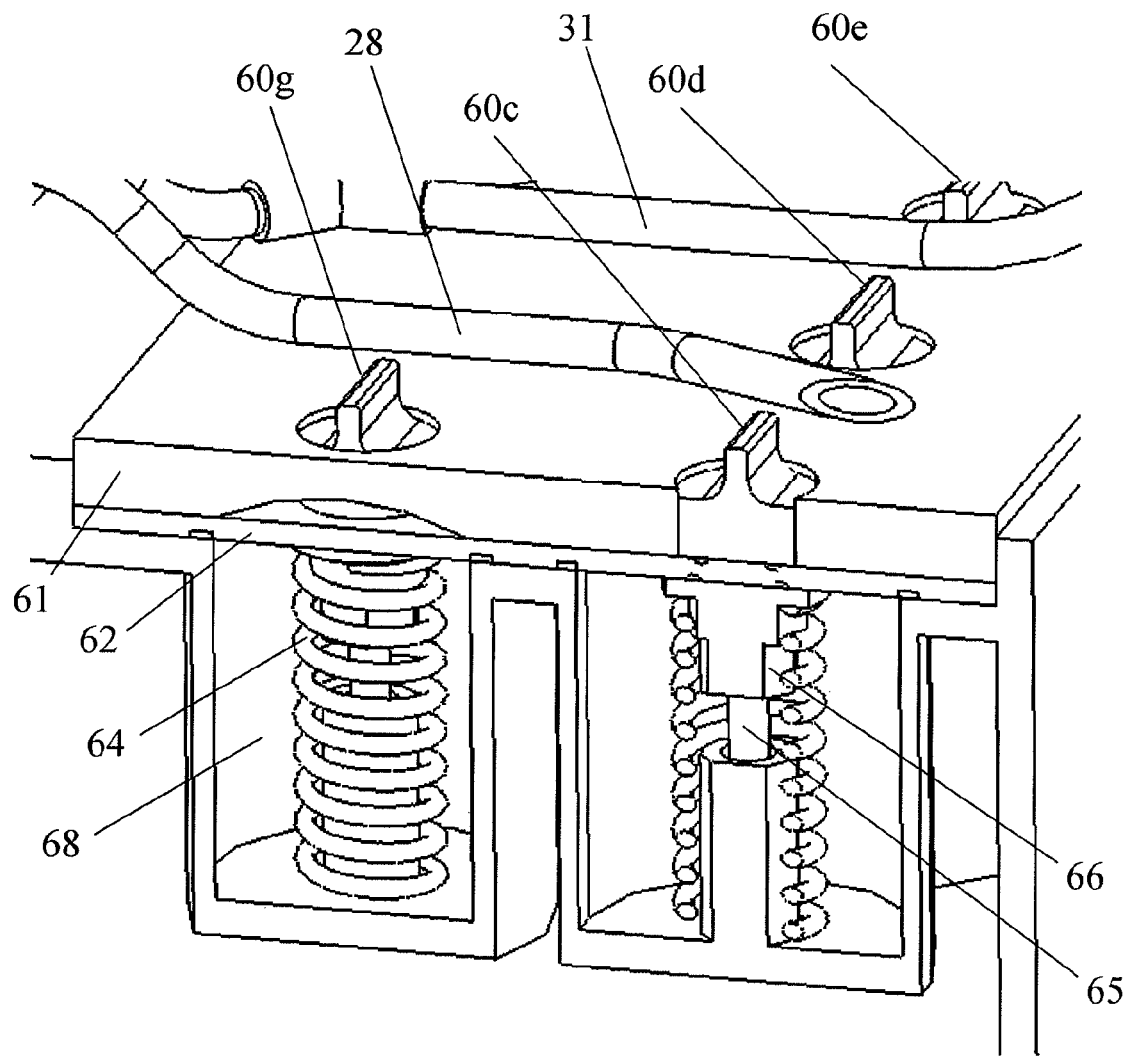
FIG. 9 is a cross sectional view of the pinch valves and tubing of FIG. 8.

FIG. 9 is a partial cross sectional view taken through the pinch valve 60$c$ and 60$g$ which are used to control the flow of fluid through the tubing element 28. The other pinch valves 60 can be similar to the pinch valves 60$c$ and 60$g$ in construction and operation. The pinch valves 60 can be spring close/vacuum open pinch valves, which are biased toward a closed position (as shown in FIG. 9) by a spring 64, and can be retracted to an open position by negative pressure. This configuration can reduce the amount of noise produced by the pinch valves as compared to a system in which the valves are biased open by one or more biasing members, (e.g., springs) and forced to a closed position by pressure (negative or positive pressure). In some embodiments, a rigid plate 61 can have holes for receiving the pinch valve plungers 60, so that only the tips of the plungers are visible to the user above the plate 61. A flexible, resilient diaphragm 62 can create a seal between the plate 61 and the actuator housing 68. Retainers, such as nuts 66, can attach the diaphragm 62 to the plungers 60, creating a seal around the guide stems 65, which can be integrally formed with the plungers 60. The springs 64 can bias the pinch valve plungers 60 towards the closed position, for example by pressing against the underside of the retainer nuts 66. The actuator housings 68 can be configured to have negative pressure selectively applied to them, for example, by a pump (not shown). When sufficient negative pressure is applied to an actuator housing 68, the biasing force of the spring 64 can be overcome and a portion of the flexible, resilient diaphragm 62 can be pulled down into the actuator housing 68, thereby compressing the spring 64 and retracting the pinch valve plunger 60 down into the open position in which fluid is allowed to flow through the corresponding tubing.

In some embodiments, the pinch valves 60 can be configured so that, when in the closed position, they can occlude PVC tubing that has an internal diameter of about 4 mm and an outer diameter of about 6 mm when fluid that has a temperature of about 10° C. is present in the tubing. The pinch valves 60 can be configured such that negative pressure of about −7 psig is able to retract the pinch valve plungers 60 to the open position. For example, the internal diameter of the actuator housings can be at least about 0.62 inches and/or less than or equal to about 0.75 inches, although values outside these ranges may also be used. By using a stronger spring 64, the pinch valve 60 can be biased more strongly toward the closed position and can be capable of occluding stronger tubing. However, if a stronger spring is used, the amount of negative pressure that is used to retract the plunger 60 also increases. If a weaker spring 64 is used than that shown in the illustrated embodiment, the less negative pressure would be needed to retract the plunger 60 but the pinch valve 60 would also have less force to occlude the tubing in the closed position. For example, springs can be selected so that the pinch valves 60 can retract under a negative pressure of at least about −7.0 psig and/or less than or equal to about −10.0 psig.

Both pinch valves 60c and 60g can isolate the patient so that replenish fluid from supply line 31 is not inadvertently delivered to the patient during the replenish phase even in the event of a failure of a single pinch valve. Similarly, both pinch valves 60b and 60f (not shown in FIG. 9) can isolate the patient when fluid is being transferred to the drain line from the interim drain bag, even in the event of a failure of a single pinch valve.

Figure 10A:
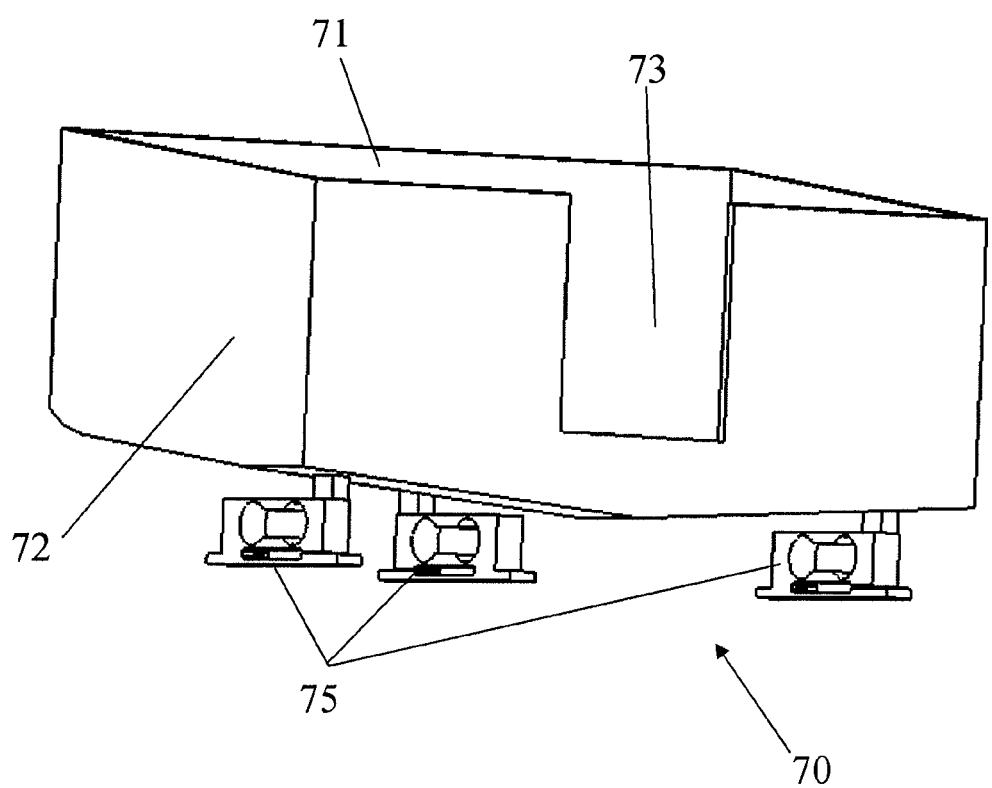
FIGS. 10A-C illustrate a heater tray assembly including load cells that are toggleable between enabled and disabled configurations.

FIG. 10A is a perspective view of an example embodiment of a heater tray assembly 70. The heater tray 72 can have walls 71 that substantially enclosed the sides and bottom of the heater tray 72, and a cutout 73 that provides a pathway to the channel 74 when the tray 72 is inserted into the APD cycler 10 as shown in FIG. 3. The bottom of the heater tray 72 can slope toward the side with cutout 73 such that when the bags 20 and 22 are placed in the heater tray 72, the fluid is urged to run towards the side with the cutout 73. The heater tray 72 can be supported by multiple (e.g., three or more) load cells 75, which can be located at the corners of a triangle such that two of the load cells are located on the lower side of the sloped bottom of the heater tray 72, since more weight would generally be applied to the lower side. Other numbers of load cells 75 can be used. For example, a single load cell 75 can be used, but would generally be exposed to more extremes in load conditions than the set of three load cells 75 shown in the illustrated embodiment. Other numbers of load cells 75 can be used, such as at least 2 load cells, 4 load cells, or 5 load cells, or more. The load cells can operate in parallel such that the measurements taken from each of the load cells is combined to provide a total weight measurement.

On or more of the load calls 75 can be toggleable between a disabled configuration in which the load cell 75 is not configured to measure weight applied to the tray 72 and an enabled configuration in which the load cell 75 is capable of measuring weight applied to the tray 72. Thus, when the APD cycler 10 is not in use, the load cells 75 can be set to the disabled configuration to prevent the load cells 75 from being damaged, for example, by relatively extreme forced that can be unintentionally applied during transportation of the APD cycler 10. When in use, the user can transition the load cells 75 to the enabled configuration.

Figure 10B:
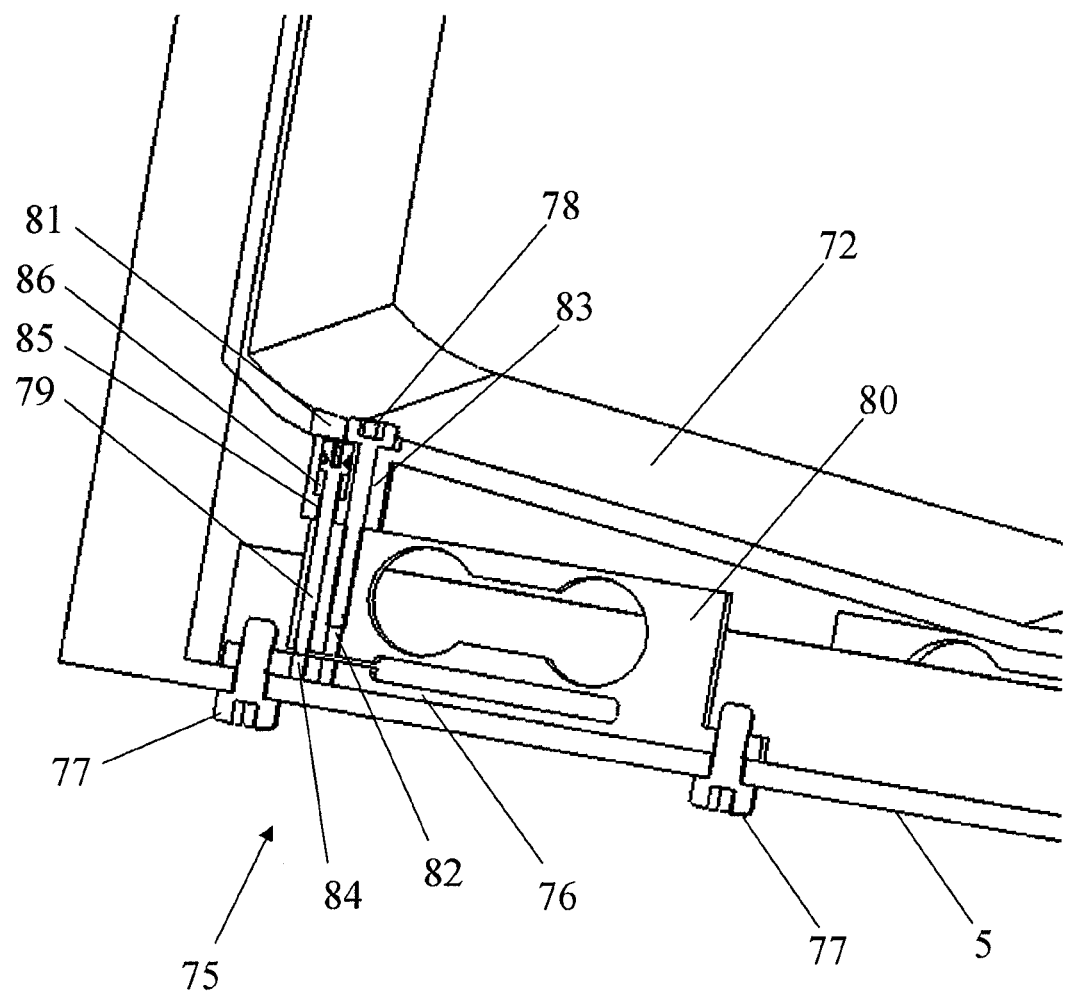

FIG. 10B is a close-up cross sectional view taken through the center of the load cell 75 on the high end of the heater tray 72. The load cell 75 can include a support bar 76 located, for example, on the underside of the load cell 75. The load cell can have a main body 80 that can be movable with respect to the support bar 76, such that when force is applied to the load cell 75, the movement of the main body 80 can apply force to a sensor, such as a strain gauge (not shown), that generates data corresponding to the force applied to the load cell 75. The support bar 76 can be secured directly to the housing 5 of the APD cycler 10 by connectors, such as screws 77. The screws 77 can have sealing members, such as O-Rings or elastomeric washers (not shown), that create a seal between the heads of the screws 77 and the housing 5 to prevent air from leaking into the containment chamber when it is evacuated to generate a negative pressure as described herein. A connector, such as screw 78, can pass through a hole 83 in the heater tray 72 and can engage a threaded bore 82 formed in the load cell 75, thereby attaching the heater tray 72 to the load cell 75. The load cell 75 can be secured to tray 72 in any other suitable manner, such as using an adhesive or snap fitting. The hole 83 can be threaded to secure the tray 72 to the load cell 75, or the hole 83 can be unthreaded and tray 72 can be secured to the load cell 75 by the head of the screw 78 abutting against the step of the recess 81 formed in the base of the heater tray 72.

A connector, such as an isolation screw 79 can be used to set the load cell to the enabled or disabled configurations. In some embodiments, the head of the isolation screw 79 can fit under the head of the screw 78. The recess 81 can be large enough to receive the isolation screw 79 in addition to the screw 78, and a channel 86 that is wide enough to receive the head of the isolation screw can be formed below the recess 81 so that the isolation screw 79 can be tightened and loosened (advanced and retracted) to toggle the load cell between the enabled and disabled configurations. In FIG. 10B, the isolation screw 79 is set to the enabled position. To set the isolation screw to the enabled position, the isolation screw can be turned in the loosening (e.g., counter-clockwise) direction. The head of the isolation screw 79 can abut against the underside of the head of the screw 78, thereby preventing the user from unintentionally loosening the isolation screw 79 to the point where it would disengage from the load cell 75. The isolation screw 79 is thus retracted to a position in which it does not engage the support bar 76. Thus, when a force is applied to the heater tray 72, the isolation screw 79 does not prevent the force from being applied to the sensor to generate a reading of the weight applied to the tray 72.

Figure 10C:
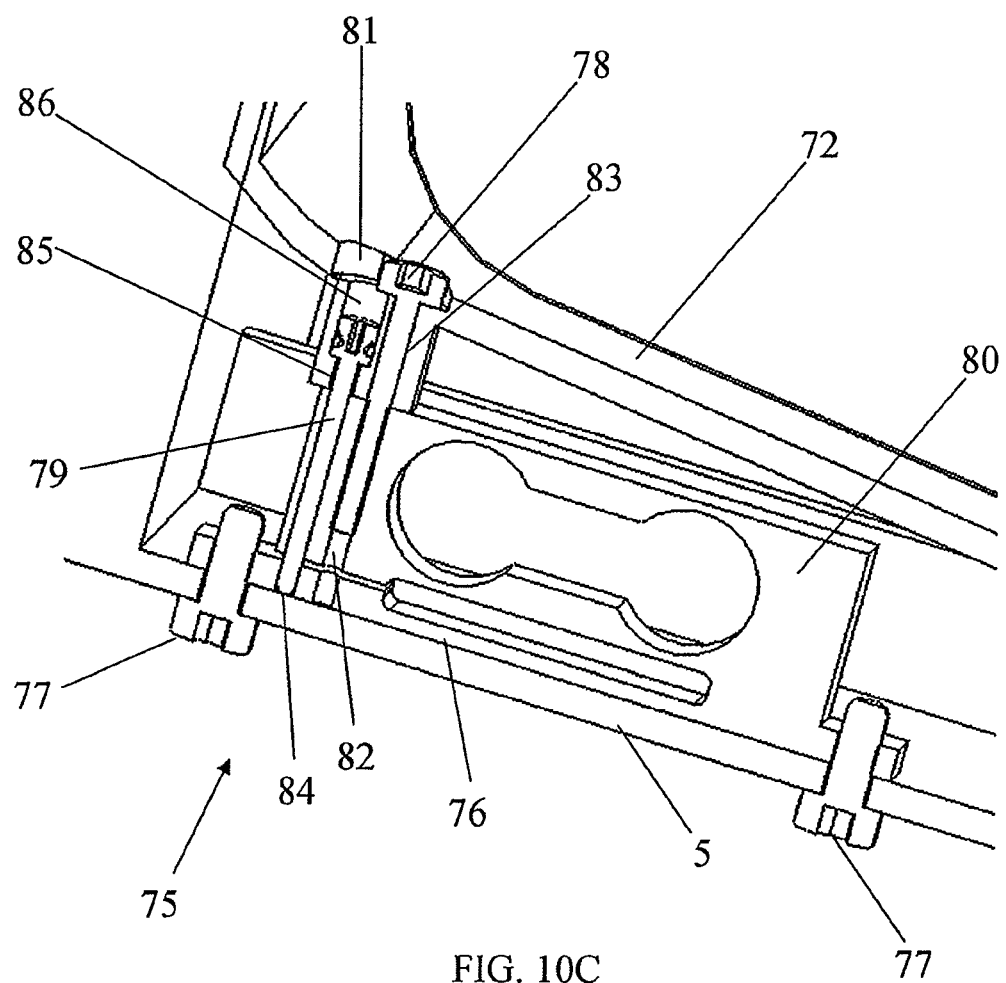

FIG. 10C is a close-up cross sectional view of the load cell 75 with the isolation screw 79 in the disabled position. The isolation screw 79 can be tightened (e.g., turned in the clockwise direction) so that the isolation screw 79 is advanced until it engages the support bar 76. The hole 85 can either be threaded or unthreaded. In some embodiments, the hole 85 is not required to be threaded. For example, the isolation screw 79 can be advance through a threaded bore 84 formed in the load cell 75 until the isolation screw is engaged with both the support bar 76 and the main body 80 portion of the load cell 75 to prevent movement therebetween and to insulate the sensor from force applied to the load cell 75. When force is applied to the heating tray 72, it is transferred though the isolation screw 79 into the support bar 76 instead of to the sensor. In some embodiments, an O-ring can be positioned between the head of the isolation screw 79 and the inner surface of the channel 86. In some embodiments, the isolation screw 79 can cause the O-ring to press tightly against the inner surface of the channel 86 to seal off the interior of the heater tray 72 from the area below the heater tray 72. Thus, if liquid is spilled into the heater tray 72, it will not leak down into the load cells 75. The screw 78 can have an O-ring or other seal, or because it is not intended to be moved during use (as is the isolation screw 79), the threads of the screw 78 can form a seal with the bore 83. The user can insert a tool (e.g. a hex screwdriver) through the recess 81 and into the channel 86 to engage the head of the isolation screw 79 to transition the isolation screw 79 between the enabled and disabled positions.

In some embodiments, during the manufacturing process, the left end of the support bar 76 is initially formed connected to left end of the main body 80 and is separated from main body 80 after the threaded bore 84 for isolation screw 79 has been drilled and tapped. Thus, the threads formed in the bore 84 in the support bar 76 can mate with the isolation screw 79 without putting any load on load cell 75.

Many alternatives are possible. For example, in some embodiments, the hole 85 at the base of the channel 86 can be threaded to secure the heater tray 72 to the isolation screw 79. Thus, when the isolation screw 79 is in the disabled position, force applied to the tray 72 is transferred through the isolation screw 79 and to the support bar 76 instead of to the sensor. In some embodiments, the isolation screw 79 can engage threads of the support bar 76 to secure the isolation screw 79 to the support bar 76 when in the disabled position, thereby preventing the isolation screw 79 (or the tray 72 which is secured to the isolation screw 79) from moving with respect to the support bar 76. In some embodiments, the isolation screw 79 is not required engage the support bar 76 but is advanced to a point where the isolation screw 79 abuts against the support bar 76, or against the housing 5, or other rigid, stationary portion of the APD cycler 10 so that force on the tray 72 does not move the tray 72 toward the load cell 75 because the force is transferred through the isolation screw 79 to the support bar 76, housing 5, or other rigid, stationary portion of the APD cycler 10. Thus, in some embodiments, the hole 85 is threaded, but the bore 84 through the load cell 75 is not required to be threaded. Also, in some embodiments, the isolation screw 79 can be displaced from the load cell 75. For example, the isolation screw 79 can pass through a threaded hole in the base of the tray 72 that is not associated with the load cell 75 (e.g., positioned adjacent to the load cell). The isolation screw 79 can be advanced until it abuts against the housing 5 below the tray 72. Thus, when a force is applied to the tray 72, the force will be carried through the isolation screw 79 to the housing 5 and not to the load cell 75.

Figure 11:
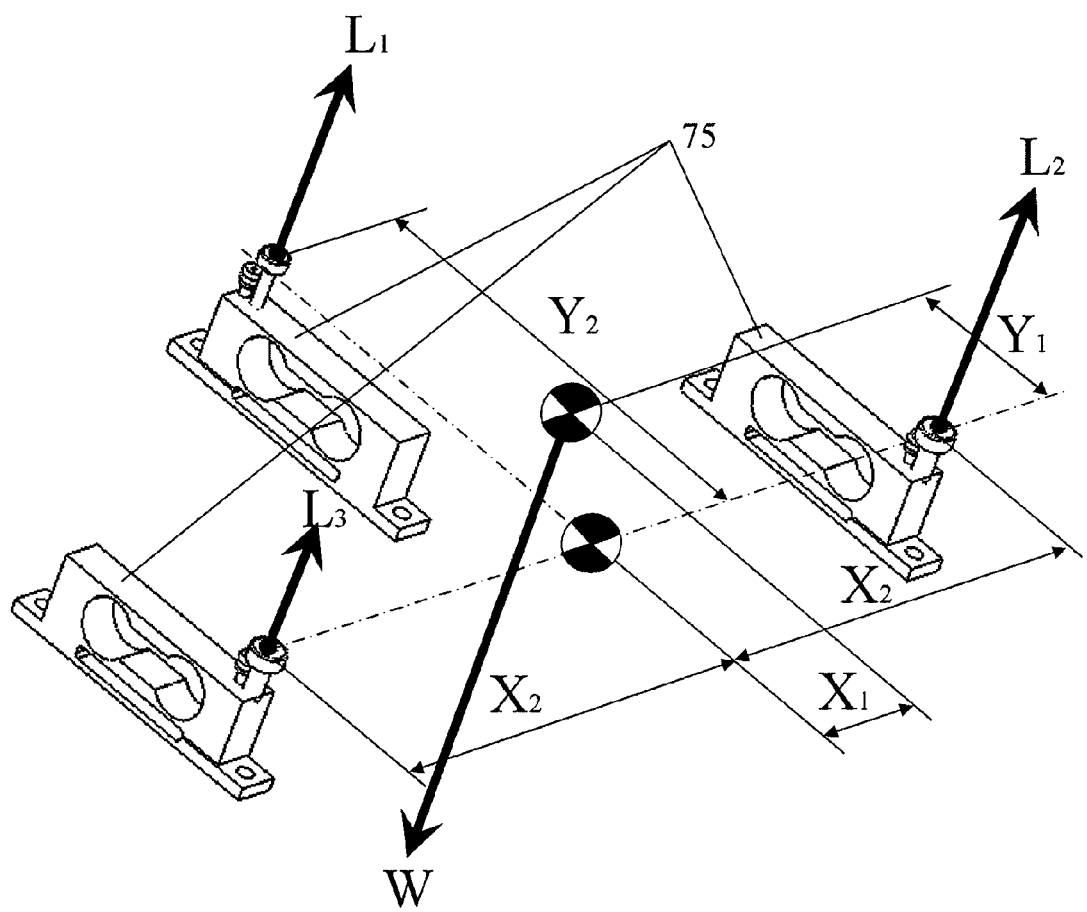
FIG. 11 schematically shows how the heater tray can transfer multiple different values of loads into the multiple load cells.

FIG. 11 schematically shows how the heater tray 72 can transfer multiple (e.g., three) different values of loads into the three load cells 75 that support the tray 72, the heater bag 20, and the interim drain bag 22. The weight of the heater tray 72 and the bags 20, 22 that it contains are represented by weight W in FIG. 11. The loads that are transmitted into the load cells 75 are represented by $L_1$, $L_2$, and $L_3$. The dimensions $X_1$ and $Y_1$ represent the distance that the center of gravity of weight W is away from the centerlines that run through the three load cells. The sum of the loads and weights equals zero and the sum of the moments about each of the centerlines through the load cells equal zero. This yields 3 equations with 3 unknowns.

$$\Sigma F = W - L_1 - L_2 - L_3 = 0 \quad \text{Equation 1}$$

$$\Sigma M_{X\text{-}Axis} = W^* Y_1 - L_1 Y_2 = 0 \quad \text{Equation 2}$$

$$\Sigma M_{Y\text{-}Axis} = W^* X_1 + L_3 X_2 - L_2 X_2 = 0 \quad \text{Equation 3}$$

These 3 equations can be solved for $L_1$, $L_2$, and $L_3$. Equation 2 can be solved directly for $L_1$.

$$L_1 = (Y_1/Y_2)^* W \quad \text{Equation 4}$$

This expression for $L_1$ can then be substituted in Equation 1 for $L_1$ so that $L_2$ can be expressed in terms of W and $L_3$ yielding the following:

$$L_2 = W - W^*(Y_1/Y_2) - L_3 \quad \text{Equation 5}$$

This expression for $L_2$ can then be substituted for $L_2$ in Equation 3 yielding $W^* X_1 + L_3^* X_2 - W^* X_2 + W^* X_2^*(Y_1/Y_2)^* + L_3^* X_2 = 0$.
Solving for $L_3$ yields the following:

$$L_3 = W^*(X_2 - X_1)/(2^* X_2) - W/2^*(Y_1/Y_2) \quad \text{Equation 6}$$

The expression for L3 in Equation 6 can be substituted for L3 in Equation 5 yielding the following:

$$L_2 = W^*(X_2 + X_1)/(2^* X_2) + W/2^*(Y_1/Y_2) \quad \text{Equation 7}$$

The geometry of the containment chamber 6 and of the solution bags 20, 22 can prevent all of the weight of the heater and drain bags 20, 22 from being placed on a single load cell. Each of load cells 75 can have a capacity of at least about 5 Kg and/or less than or equal to about 20 Kg, although other values outside these ranges may also be used. In some embodiments, the load cells 75 can each have a nominal capacity of about 10 Kg with a safe overload of about 15 Kg and be suitable for use in this application. In some examples, a maximum fluid volume that would fit into the containment chamber can occur at after the initial drain stage at the start of the therapy. For example, the patient may have an initial drain volume of twice their prescribed fill volume (e.g., 3000 ml) resulting in an initial drain of 6000 ml, and a full 6 liter heater bag may be present in the APD cycler 10 as well. This 12 liter (about 12 kg) load would be distributed across the three load cells per equations 4, 6, and 7 based upon the location of the combined center of gravity of the heater tray 72, the heater bag 20 and the interim drain bag 22.

In some embodiments, the APD cycler can use the load cells 75 to measure the amount of the fluid contained within the heater bag 20 and/or the drain bag 22. Thus, as the heater bag 20 is filled with fresh dialysis solution, the load cells 75 can measure the amount of fluid in the heater bag 20 and the system can cease filling the heater bag 20 when the desired volume of fluid is contained therein. The load cells 75 can also measure the weight of the fluid as it is transferred from the heater bag 20 to the patient, and the patient fill stage can end when the desired volume of fluid is transferred to the patient. Similarly, the load cells 75 can measure the weight of the spent dialysate and accompanying ultrafiltration fluid that is from the patient into the drain bag 22, and when the drain stage is complete, the system can measure the amount of fluid drained from the patient. Thus, the amount of ultrafiltration can be measured. Then the fluid can be drained from the drain bag 22 to exit the ADP cycler 10. Thus, the drain bag 22 can be an intermediate drain bag 22 since the fluid is first drained to the intermediate drain bag 22 to be measured, and it is then drained from the system after measurement. Likewise, the heater bag 20 can serve not only the purpose of providing a reservoir for heating the fluid, but can also serve as an intermediate fill bag for measuring the fresh fluid before it is delivered to the patient.

In some embodiments, the APD cycler 10 can use a backup volume monitor to measure the volumes of fluid that are delivered to the patient and/or drained from the patient. The backup volume monitor can be used to confirm measurements made by load cells 75. In some embodiments, the backup volume monitor can use negative (sub-atmospheric) pressure and make calculations based on the ideal gas law. In some embodiments, the accuracy of the backup volume monitor has a lower level of accuracy as compared to primary monitoring system (e.g, load cells 75), and the backup volume monitor can be used to verify that the primary monitoring system (e.g., load cells 75) are functioning properly.

Figure 12:
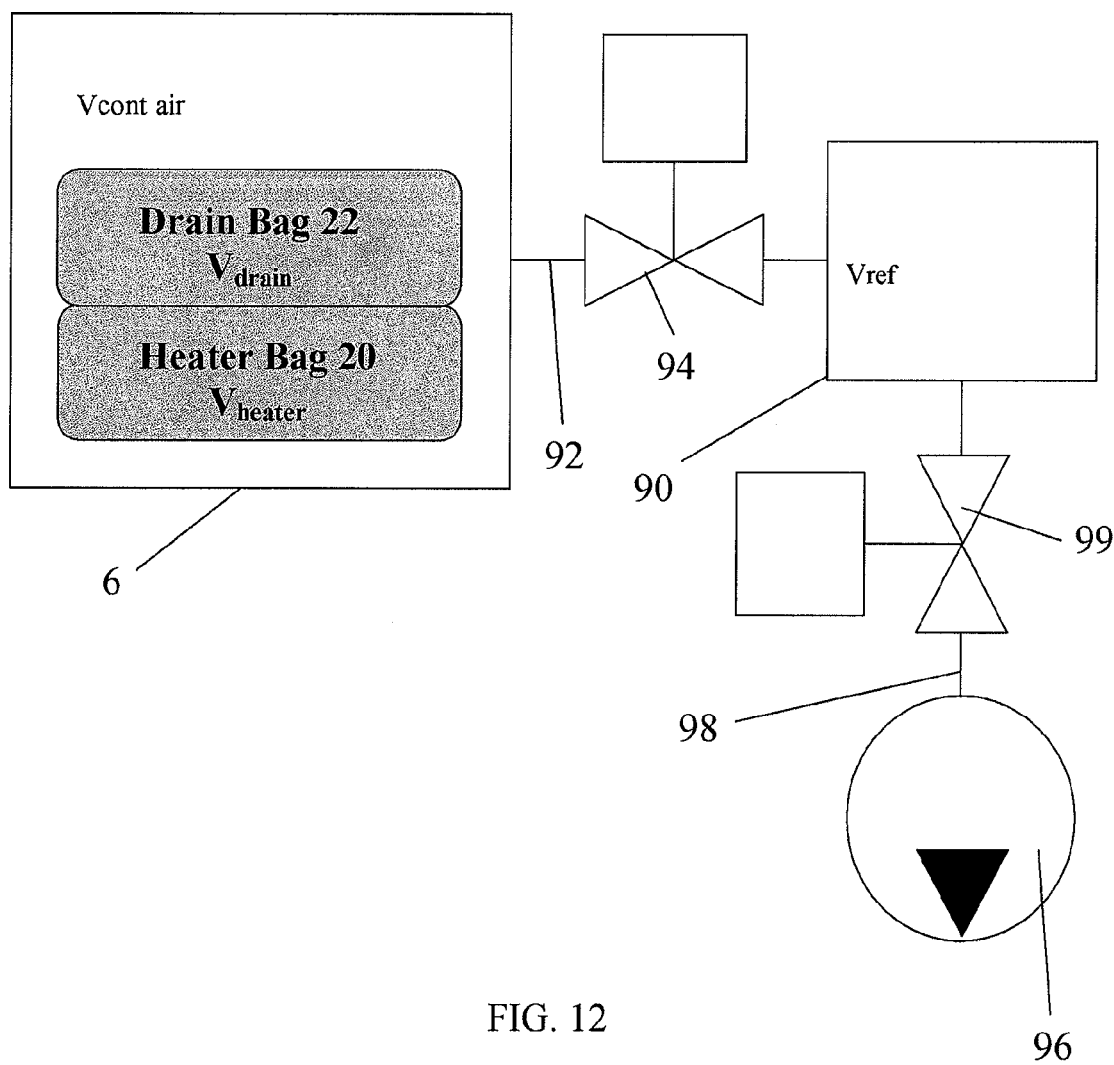
FIG. 12 schematically shows an example embodiment of a pressure-based volume measurement system that can be used by the APD cycler of FIG. 1.

FIG. 12 is schematic representation of an example embodiment of an implementation of the pressure-based volume measurement system that can be used by the APD cycler 10. As described herein, the containment chamber 6 can be sealed so that a negative pressure can be maintained therein. The containment chamber can have a total volume $V_{cont}$. The heater bag 20 and drain bag 22 can be positioned inside the containment chamber 6. The heater bag 20 can contain a volume of fluid $V_{heater}$, and the drain bag 22 can contain a volume of fluid $V_{drain}$, so that the volume of air inside the containment chamber 6 $V_{cont\ air}$ is equal to $V_{cont}$-$V_{heater}$-$V_{drain}$. A reference chamber 90 can have a volume $V_{ref}$ and can also be sealable to maintain negative pressure therein. The reference chamber 90 can be connected to the containment chamber 6 by a pathway 92. A valve 94 can be positioned on the pathway 92 such that the pathway can be selectively opened and closed. A vacuum pump 96 can be connected to the reference chamber 90 via a pathway 98. A valve 99 can selectively open and close the pathway 98.

Negative pressure can be applied to the containment chamber 6 by opening the valves 94 and 99 and running the vacuum pump 96 until the desired negative pressure is achieved. Then the valve 94 can be closed sealing the negative pressure within the containment chamber 6. Negative pressure can be applied to the reference chamber 90 by closing the valve 94 and opening the valve 99 and running the vacuum pump 96 until the desired negative pressure is achieved. Then the valve 99 can be closed to seal the negative pressure within the reference chamber 90. Thus, the containment chamber 6 and the reference chamber 90 can be independently set to different negative pressures. The containment chamber 6 and the reference chamber 90 can each have one or more pressure sensors to measure the pressure contained therein. Various suitable pressure sensors can be used. For example, Motorola's Freescale MPX2053 and MPX2010 differential pressure sensors or Fujikura's XFDM differential pressure sensors can be used measuring the pressure of the containment chamber 6 and the reference chamber 90 during pressure measurements.

Many alternatives are possible. For example, a separate pathway can connect the vacuum pump 96 to the containment chamber 6 and a valve can selectively open and close that separate pathway. In this embodiment, negative pressure can applied to the containment chamber 6 without opening the reference chamber 90. In some embodiments, the reference chamber 90 and containment chamber 6 can have independent vacuum pumps. Although much of the description herein describes negative (sub-atmospheric) pressure being applied to the containment chamber 6 and reference chamber 90, in some embodiments, the pump 96 can be used to apply positive pressure to the containment chamber 6 and/or to the reference chamber 90.

Figure 13:
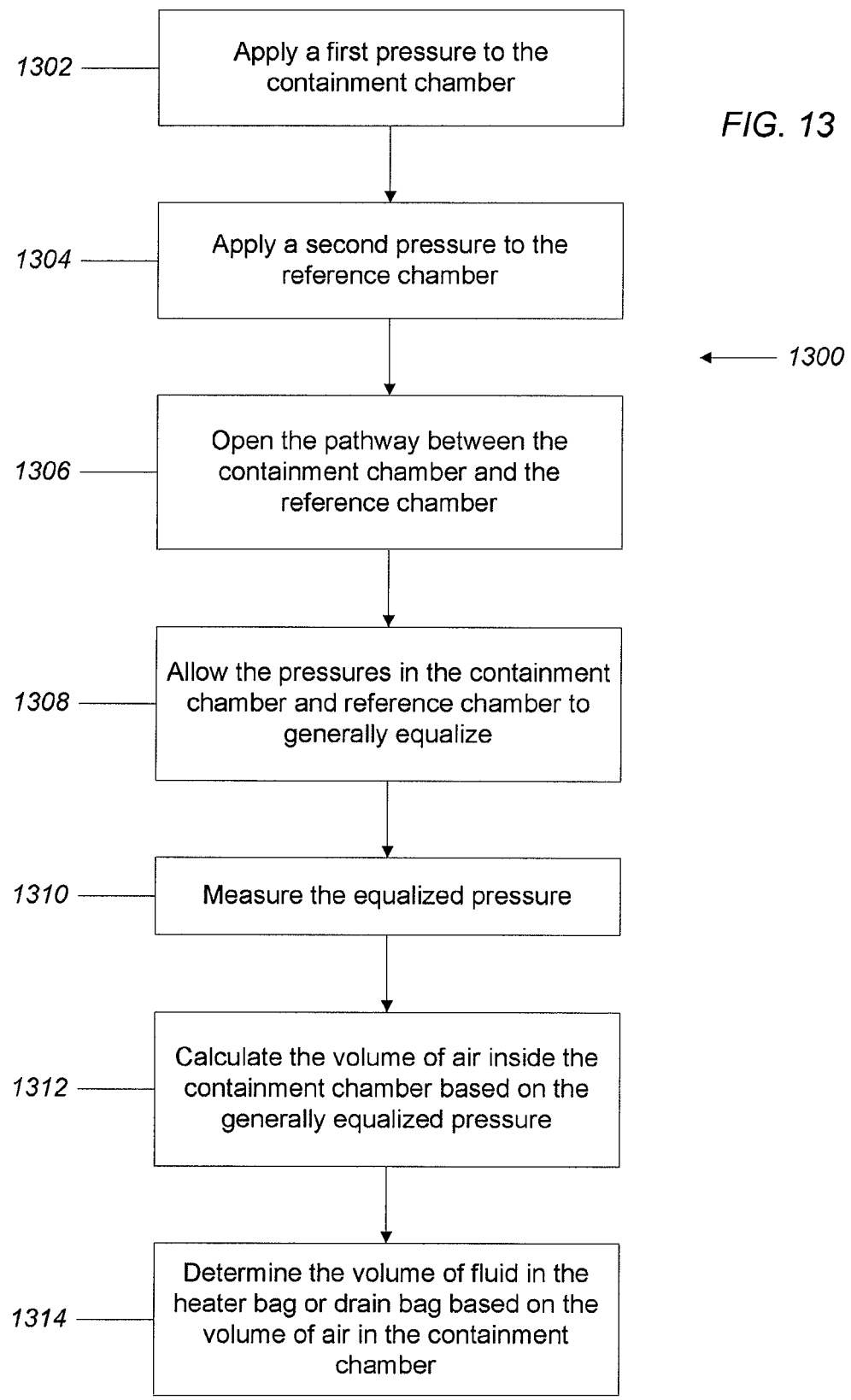
FIG. 13 is a flowchart that shows an example embodiment of a method of determining a volume of fluid using the pressure-based measurement system of FIG. 12.

FIG. 13 is a flowchart that shows and example embodiment of a method 1300 for determining the volume of the fluid contained in the heater bag 20 or drain bag 22. At block 1302, a first pressure $P_{1cont}$ is applied to the containment chamber. In some embodiments, the pressure $P_{1cont}$ can be at least about −0.1 psig and/or less than or equal to about −1.0 psig. An example of a suitable pressure is about −0.5 psig. Other values outside these ranges may also be used. Although several examples provided herein are described using a pressure of −0.5 psig to the containment chamber 6, other pressures can be used. In some cases, the pressure $P_{1cont}$ can be set to about 0.0 psig, by, for example, venting the containment chamber to the pressure outside the APD cycler 10. In some embodiments, a positive or negative pressure is used for $P_{1cont}$ so test whether the containment chamber 6 is sealed properly. For example, if $P_{1cont}$ were intentionally set to atmospheric pressure, the system would not be able to detect leakage from the containment chamber. Thus, in some embodiments, the containment chamber 6 is maintained as a non-atmospheric pressure (e.g., a negative pressure such as −0.1 psig or more) during the use. At block 1304, a second pressure $P_{1ref}$ is applied to the reference chamber 90. The pressure $P_{1ref}$ can be at least about −5.0 psig and/or less than or equal to about −9.0 psig, and can be about −7.0 psig, although other pressures outside these ranges can be used. In some embodiments, the pressure $P_{1ref}$ is set to a more negative pressure than $P_{1cont}$. For example, $P_{1ref}$ can be set to a negative pressure value that is 5 times or 10 time or 20 times greater (in the negative direction) than $P_{1cont}$. Other multipliers can be used.

At block 1306, the valve 94 is opened and, at block 1308, the pressures in the containment chamber 6 and the reference chamber 90 equalize through the pathway 92. At block 1310, the substantially equalized pressure is measured. The equalized pressure can be recorded in some embodiments. For example, the APD cycler 10 can include a controller that comprises a computer readable storage medium (non-transitory storage medium). The equalized pressure can be recorded in the computer readable medium. In some cases, the equalized pressure is stored for later reference, and in some cases the equalized pressure can be stored for only as long as needed to make the other calculations, as described herein.

At block 1312, the volume of air inside the containment chamber is calculated based on the equalized pressure. When the pressure $P_{1ref}$ is set to a more negative pressure than $P_{1cont}$, generally, after pressure equalization, the equalized pressure will generally be lower as the volume $V_{cont\ air}$ increases, because a larger volume of air inside the containment chamber 6 will have more air available to move into the reference chamber 90 to compensate for the higher negative pressure therein. In some cases, the computer readable medium can contain a lookup table that includes air volume values that correspond to equalized pressure values. The controller can use the lookup table to identify the $V_{cont\ air}$ value that corresponds to the measured equalized pressure. In some embodiments, the controller can comprise a formula or algorithm for calculating the $V_{cont\ air}$ from the measured equalized pressure. The lookup table and/or formula can be generated from or confirmed with actually measured values previously made. One example formula that can be used is as follows:

$$V_{cont\ air} = (P_{2Ref} - P_{1Ref})/(P_{1Cont} - P_{2Cont}) * V_{Ref}$$

The measurement can be performed substantially isothermally with the air temperatures maintained at a constant value. Thus, the APD cycler 10 can have a temperature sensor and heating and/or cooling elements for controlling the temperature inside the APD cycler 10. In some embodiments, the temperature sensor and heating element used for heating fluid inside the heating bag 20 can be used, although other dedicated sensors and heating and/or cooling elements can be used. It is noted that the temperature is not required to remain substantially constant during the entire process, so long as the temperature is substantially the same at block 1310 (when the equalized pressure is measured) as it is at blocks 1302 and 1304 when the pressures of the containment chamber 6 and reference chamber 90 are set. In some embodiments, a threshold level of temperature difference is considered acceptable, such as, for example, about 2° C., 1° C., 0.5° C., or less. Other threshold acceptable temperature differences may be used as well. In some cases, the process can be performed quickly (substantially adiabatically) so that essentially no thermal energy is transferred from the gases being used. Thus, in some embodiments, the calculations can be based on Boyle's law in which temperature is substantially constant. In some embodiments, the temperature is not controlled and is not assumed to be constant. Rather, temperature measurements can be taken (e.g., using one or more temperature sensors configured to measure the temperature in the containment chamber 6 and/or the reference chamber 90) and considered in making the calculation of the $V_{cont\ air}$. One example formula that can be used is as follows:

$$V_{cont\ air} = V_{Ref}\left(\left(\frac{P_{2Ref}}{T_{2Ref}} - \frac{P_{1Ref}}{T_{1Ref}}\right)/\left(\frac{P_{1Cont}}{T_{1Cont}} - \frac{P_{2Cont}}{T_{2Cont}}\right)\right)$$

At block 1314, the volume of fluid in the heater bag 20 or the drain bag 22 can be determined from the calculated volume of air inside the containment chamber $6 V_{cont\ air}$ using the equation $V_{cont\ air} = V_{cont} V_{heater} - V_{drain}$. If $V_{heater}$ is known, then $V_{drain}$ can be determined, and if $V_{drain}$ is known, then $V_{heater}$ can be determined. Thus, in some embodiments, during the operation of the APD cycler, the volume of fluid inside the heater bag 20 and the volume of fluid inside the drain bag 22 are not both changed in between sequential pressure measurements made using the pressure-based volume monitoring system.

In some embodiments, the volume $V_{ref}$ of the reference chamber 90 can be at least about 0.25 liters and/or less than or equal to about 5.0 liters. Some examples of $V_{ref}$ can be about 0.5 liters, 1.0 liter, 2.0 liters, or 3.0 liters. Other values outside of these ranges can be used. In some embodiments, a low volume reference volume can be used to keep the size of the APD cycler 10 relatively compact in size so that it can be easily transported (e.g., fitting into an airplane overhead compartment to facilitate travel by the user). The maximum volume of the heater bag 20 and the drain bag 22 can be of the same size or of different sizes, and each be at least about 2 liters and/or less than or equal to about 10 liters, and can be about 6 liters, although values outside these ranges may also be used. For example, if the heater bag 20 is not configured to be replenished (e.g., supply lines 31 and 32 omitted), then the maximum volume of the heater bag 20 may be larger than 10 liters. The volume of the containment chamber 6 can be at least about 5 liters and/or less than or equal to about 20 liters, and can be about 16 liters in some cases, although other values outside these ranges can be used.

Table 1 contains calculations made using embodiments having the reference chambers 90 of volumes of 0.5 liters, 1.0 liter, 2.0 liters, and 3.0 liters in which the reference chamber was evacuated to −7.0 psig. The containment chamber 6 having a volume of 16 liters was used and measurements were made with both the heater bag 20 and drain bag having 3 liters of fluid therein, resulting in a $V_{cont\ air}$ value of 10 liters, and also with the heater bag 20 empty with 3 liters of fluid in the drain bag, resulting in a $V_{cont\ air}$ of 13 liters. The containment chamber 6 was evacuated to about −0.5 psig. The two pressures were allowed to equilibrate as described herein, and the pressure changes are shown in Table 1. Using a reference volume of 3 liters, the difference in equalized pressure for an empty heater bag 20 versus a heater bag 20 containing 3.0 liters of fluid is 1.5 psi−1.2188 psi=0.2812 psi. This indicates that an inaccuracy in pressure reading of 0.001 psi now corresponds to a fluid measurement error of about 10 grams, or about 10 ml. The volumes and pressures can be adjusted to provide a system which is more or less sensitive to error and/or which exposes the APD cycler 10 to more or less negative pressure.

In some embodiments, the negative pressure inside the containment chamber does not exceed a maximum negative value of about −2.0 psig. Thus, the containment chamber 6 does not need to be constructed to withstand high negative pressures larger than −2.0 psig, thereby reducing the size, and weight, and cost of manufacturing for the APD cycler 10, and allowing the APD cycler 10 to be used as a gravity/vacuum APD cycler 10 in which the containment chamber 10 has O-rings and/or seals which may not be capable of reliably withstanding extreme negative pressures, for example, as described herein. Other configurations of APD cyclers can be used. In some embodiments, the reference chamber 90 can be exposed to high levels of negative pressure (e.g., −7.0 psig), and the reference chamber 90 can be constructed to more easily withstand high negative pressure than can the containment chamber 6 because the reference chamber is a simpler structure (e.g., not having a hinging cover to allow the user access to the interior, and/or not having flexible tubes and bolts exiting the chamber with O-rings and seals). Applying a relatively low negative pressure to the containment chamber can also result in less noise during operation of the APD cycler 10, as compared to a system that applies a higher negative pressure therein.

Table 2 contains calculations made using reference chambers 90 of volumes of 0.5 liters, 1.0 liter, 2.0 liters, and 3.0 liters in which the reference chamber 90 was vented to atmospheric pressure instead of being brought to a negative pressure. A containment chamber 6 with a volume of 16 liters was used and measurements were made with both the heater bag 20 and drain bag having 3 liters of fluid therein, resulting in a $V_{cont\ air}$ value of 10 liters, and also with the heater bag 20 empty with 3 liters of fluid in the drain bag, resulting in a $V_{cont\ air}$ of 13 liters. The containment chamber 6 was evacuated to about −1.5 psig. The two pressures were allowed to equilibrate, and the pressure changes are shown in Table 2. Using a reference volume of 3 liters, the difference in equalized pressure for an empty heater bag 20 versus a heater bag 20 containing 3.0 liters of fluid is 0.3462 psi−0.2813 psi=0.0649 psi. This indicates that an inaccuracy in pressure reading of 0.001 psi now corresponds to a fluid measurement error of about 50 grams (or about 50 ml), which in some cases may be unacceptable to the dialysis community. However, this embodiment does not expose the APD cycler to negative pressures of over 1.5 psig.

TABLE 1

Boyle's Law with −7 psig Vacuum Applied to the Reference Chamber

| Delta $P_{ref}$ | Delta $P_{Cont}$ | $V_{airCont}$ | $P_{2ref}$ | $P_{1ref}$ | $P_{1Cont}$ | $P_{2Cont}$ | $V_{ref}$ |
|---|---|---|---|---|---|---|---|
| 6.1905 | −0.3095 | 10.0000 | −0.8095 | −7.0000 | −0.5000 | −0.8095 | 0.5000 |
| 5.9091 | −0.5909 | 10.0000 | −1.0909 | −7.0000 | −0.5000 | −1.0909 | 1.0000 |
| 5.4167 | −1.0833 | 10.0000 | −1.5833 | −7.0000 | −0.5000 | −1.5833 | 2.0000 |
| 5.0000 | −1.5000 | 10.0000 | −2.0000 | −7.0000 | −0.5000 | −2.0000 | 3.0000 |
| 6.2593 | −0.2407 | 13.0000 | −0.7407 | −7.0000 | −0.5000 | −0.7407 | 0.5000 |
| 6.0357 | −0.4643 | 13.0000 | −0.9643 | −7.0000 | −0.5000 | −0.9643 | 1.0000 |
| 5.6333 | −0.8667 | 13.0000 | −1.3667 | −7.0000 | −0.5000 | −1.3667 | 2.0000 |
| 5.2813 | −1.2188 | 13.0000 | −1.7188 | −7.0000 | −0.5000 | −1.7188 | 3.0000 |

TABLE 2

Boyle's Law with −1.5 psig Vacuum in the Containment Chamber

| Delta $P_{ref}$ | Delta $P_{Cont}$ | $V_{airCont}$ | $P_{2ref}$ | $P_{1ref}$ | $P_{1Cont}$ | $P_{2Cont}$ | $V_{ref}$ |
|---|---|---|---|---|---|---|---|
| −1.4286 | 0.0714 | 10.0000 | −1.4286 | 0.0000 | −1.5000 | −1.4286 | 0.5000 |
| −1.3636 | 0.1364 | 10.0000 | −1.3636 | 0.0000 | −1.5000 | −1.3636 | 1.0000 |
| −1.2500 | 0.2500 | 10.0000 | −1.2500 | 0.0000 | −1.5000 | −1.2500 | 2.0000 |
| −1.1538 | 0.3462 | 10.0000 | −1.1538 | 0.0000 | −1.5000 | −1.1538 | 3.0000 |
| −1.4444 | 0.0556 | 13.0000 | −1.4444 | 0.0000 | −1.5000 | −1.4444 | 0.5000 |
| −1.3929 | 0.1071 | 13.0000 | −1.3929 | 0.0000 | −1.5000 | −1.3929 | 1.0000 |
| −1.3000 | 0.2000 | 13.0000 | 1.3000 | 0.0000 | 1.5000 | 1.3000 | 2.0000 |
| −1.2188 | 0.2813 | 13.0000 | 1.2188 | 0.0000 | 1.5000 | 1.2188 | 3.0000 |

Table 3 contains calculations made using reference chambers 90 of volumes of 0.5 liters, 1.0 liter, 2.0 liters, and 3.0 liters in which the reference chamber 90 was vented to atmospheric pressure instead of being brought to a negative pressure. The containment chamber 6 had a volume of 16 liters was used and measurements were made with both the heater bag 20 and drain bag having 3 liters of fluid therein, resulting in a $V_{cont\,air}$ value of 10 liters, and also with the heater bag 20 empty with 3 liters of fluid in the drain bag, resulting in a $V_{cont\,air}$ of 13 liters. The containment chamber 6 was evacuated to about −7.0 psig. The two pressures were allowed to equilibrate, and the pressure changes are shown in Table 3. Using a reference volume of 3 liters, the difference in equalized pressure for an empty heater bag 20 versus a heater bag 20 containing 3.0 liters of fluid is 1.6154 psi−1.3125 psi=0.3029 psi. This indicates that an inaccuracy in pressure reading of 0.001 psi now corresponds to a fluid measurement error of about 10 grams (about 10 ml).

TABLE 3

Boyle's Law with −7 psig Vacuum in Containment Chamber

| Delta $P_{ref}$ | Delta $P_{Cont}$ | $V_{airCont}$ | $P_{2ref}$ | $P_{1ref}$ | $P_{1Cont}$ | $P_{2Cont}$ | $V_{ref}$ |
|---|---|---|---|---|---|---|---|
| −6.6667 | 0.3333 | 10.0000 | −6.6667 | 0.0000 | −7.0000 | −6.6667 | 0.5000 |
| −6.3636 | 0.6364 | 10.0000 | −6.3636 | 0.0000 | −7.0000 | −6.3636 | 1.0000 |
| −5.8333 | 1.1667 | 10.0000 | −5.8333 | 0.0000 | −7.0000 | −5.8333 | 2.0000 |
| −5.3846 | 1.6154 | 10.0000 | −5.3846 | 0.0000 | −7.0000 | −5.3846 | 3.0000 |
| −6.7407 | 0.2593 | 13.0000 | −6.7407 | 0.0000 | −7.0000 | −6.7407 | 0.5000 |
| −6.5000 | 0.5000 | 13.0000 | −6.5000 | 0.0000 | −7.0000 | −6.5000 | 1.0000 |
| −6.0667 | 0.9333 | 13.0000 | −6.0667 | 0.0000 | −7.0000 | −6.0667 | 2.0000 |
| −5.6875 | 1.3125 | 13.0000 | −5.6875 | 0.0000 | −7.0000 | −5.6875 | 3.0000 |

Although many of the example embodiments described herein disclose the use of negative pressure applied to the containment chamber 6 and/or to the reference chamber 90, in some embodiments, positive pressure may be used. In some embodiments, the negative pressure applied to the containment chamber 6 can be used not only for determining the volume of fluid being transferred, but also to draw fluid into the containment chamber 6, such as when draining fluid from a patient, as described herein. In some cases, the use of negative pressure, instead of positive pressure, can reduce occurrence of problems during treatment, such as air being pushed into the bags 20 and 22 by positive pressure or unintentional overfilling due to force applied on the bags 20 and 22 by positive pressure.

Figure 14:
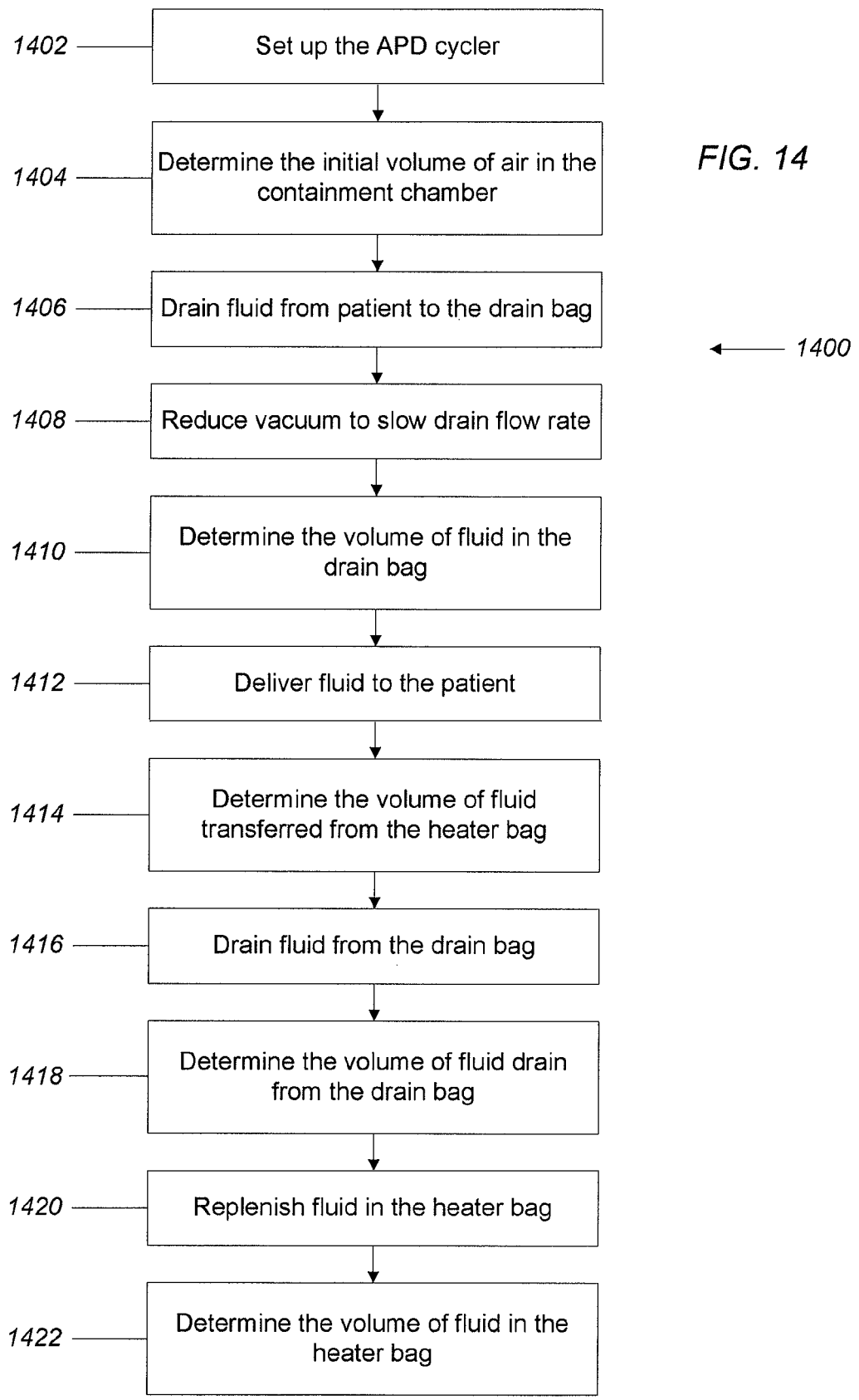
FIG. 14 is a flowchart that shows an example embodiment of a method of applying an automated peritoneal dialysis treatment to a patient.

FIG. 14 is a flowchart that schematically illustrates an example embodiment of a method 1400 of treating a patient, for example, by performing automated peritoneal dialysis (APD). At block 1402, the APD cycler 10 is set up. The heater bag 20 and the interim drain bag 22 can be placed into the heater tray 72, and the disposable set 30 can be loaded, for example, as described herein. The system can perform line priming and integrity testing of the disposable set 30 and any other suitable preliminary set up procedures. In some cases, a filled heater bag 20 is placed on the heater tray 72 in order to reduce therapy costs and to minimize the time before the therapy can begin. However, a partially filed, or even an empty bag can be placed on the heater bag when two or more solutions are mixed (e.g., introduce through the supply lines 31 and 32) to form a solution that has, for example, an intermediate Dextrose concentration.

At block 1404, the system can determine the initial volume of air in the containment camber. The containment chamber can be set to a first pressure (e.g, about −0.5 psig). The reference chamber can be set to a second pressure (e.g., about −7 psig). The pressures can be allowed to equalize and the initial volume of the air in the containment chamber can be calculated as described herein (e.g., using Boyle's Law). This can be used to determine the initial volume of fluid, if any, in the heater bag 20.

In some embodiments, the equalized pressure in the containment chamber 6 is at a negative pressure (e.g., about −1.5 psig) after equalization. The negative pressure can be used to draw fluid into the drain bag 20 for the initial drain at block 1406. Pinch valves 60b and 60f are opened and fluid is drain through patient line coil 34 past open pinch valve 60b, past open pinch valve 60f, through tubing 27, through sealing Y connector 33a, through tubing 39, and into the interim drain bag 22. In some embodiments, the negative pressure in the containment chamber 6 can be adjusted before or during the drain to regulate the drainage of fluid.

The load cells 75, under the heater tray 72, can measure the change in weight of the interim drain bag 20 and provide continuous feedback to the controller of the APD cycler 10. The controller can calculate the flow rate of fluid into the drain bag 22. The fluid flow rate typically can initially be generally between about 125 and 250 ml/min, or can be less than or equal to about 200 ml/min, for example, and can generally start to slow down as the patient's peritoneum empties of fluid. At block 1408, the controller can recognize when the flow rate has dropped below a threshold value, or some other indicator that the drain of the patient's peritoneum is nearing completion, and in response the controller can reduce the negative pressure inside the containment chamber 6 towards the end of the drain when the flow rate slows and approaches the "no flow" state. The negative pressure can be released gradually as the flow rate slow or can be released relatively quickly. In some embodiments, the negative pressure can be reduced to a value of at least about −0.5 and/or less than or equal to −1.2 when the flow rate drops below a "low flow" rate. The pressure can be set to values outside these ranges when the "low flow" rate is reached. Reducing the pressure at the end of the drain can reduce the level of pain or discomfort experienced by the patient when negative pressure is applied to the patient's peritoneum when little or no fluid is left to drain. The negative pressure can be maintained substantially constant until the fluid flow naturally slows, at which time the negative pressure can be reduced to further slow the flow rate until the lowest pressure is applied at the end of the drain as the flow rate stops. This differs from the gradual reduction in suction pressure that naturally occurs with gravity based drainage as the fluid level in the interim drain bag gradually rises as it fills, gradually reducing the drain suction throughout the entire drain phase.

A "slow flow" threshold can be set to trigger the reduction of the negative pressure. A "slow flow" event can be triggered (causing a reduction in pressure) if the flow rate remains below the "slow flow" rate for a predetermined time, such as at least about 1 minute and/or less than or equal to about 10 minutes; or at least about 3 minutes and/or less than or equal to about 6 minutes. A "no flow" threshold can be set to trigger the stop of the drain stage (e.g., by closing the pinch valves 60*b* and 60*f*. A "no flow" event can be triggered (causing a termination of the drain stage) if the flow rate remains below the "slow flow" rate for a predetermined time, such as at least about 1 minute and/or less than or equal to about 10 minutes; or at least about 3 minutes and/or less than or equal to about 6 minutes. In some embodiments, the "slow flow" and "no flow" thresholds are adjustable. For example, the default "slow flow" flow rate threshold for an adult patient with a 2000 ml fill volume could be 2% of the fill volume or 40 ml/min and the default flow rate threshold for "no flow" could be 0.5% of the 2000 ml fill volume or 10 ml/min. These values could be decreased to 32 ml/min and 8 ml/min, 20 ml/min and 5 ml/min, or 16 ml/min and 4 ml/min if the patient drained slower than normal. The same is true for non-adult patients wherein, for example, the default "slow flow" flow rate threshold for an adolescent patient with 1000 ml fill volume could be 2% of the fill volume or 20 ml/min and the default flow rate threshold for "no flow" could be 0.5% of the 1000 ml fill volume or 5 ml/min. These values could be decreased to 16 ml/min and 4 ml/min, 12 ml/min and 3 ml/min, or 8 ml/min and 2 ml/min if the patient drained slower than normal. In some embodiments, the "slow flow" threshold can be at least about 5 ml/min and/or less than or equal to about 50 ml/min. Values outside these ranges can be used. In some embodiments, the "no flow" rate can be at least about 1 ml/min and/or less than or equal to about 15 ml/min. Values outside these ranges can be used.

When the drain phase ends, pinch valves 60*a* and 60*f* can close and the volume of fluid drained, as measured by the load cells, can be recorded. At block 1410, the volume of fluid in the drain bag 22 can be determined using the pressure-based system. The vacuum in containment chamber 6 can be set to a first value (e.g., decreased to about −0.5 psig) and the vacuum in the reference chamber 90 (3 liter size) can be set to a second value (e.g., increased to about −7 psig). After the two pressures are recorded, the two chambers can be connected and the pressure within can be allowed to equalize. The new pressure readings can be recorded and used along with the previous pressure readings and the previously calculated pre-drain containment chamber air volume to calculate the volume of fluid that was drawn into the containment chamber 6 during drain. If the fluid volume as measured by the load cells differs by more than a threshold amount or percentage (e.g., 10%) from that calculated using the pressure-based system, an alarm will be posted. Thus, if the volume measured by the pressure-based system is between 90% and 110% of the value that was reported by the load cell system, the therapy can continue. If it is not, an alarm can be posted. Other error tolerance percentages may be used, such as, for example, any suitable value that is at least about 3% and/or less than or equal to about 15%.

If no alarm was posted, the post drain containment chamber air volume can be recorded and fluid can be delivered to the patient from the heater bag at block 1412. In some embodiments, the temperature is measured to determine if the fluid is of a suitable temperature for delivery to the patient, and the temperature of the fluid may be adjusted if needed. The vacuum in containment chamber 6 can be set to about −0.1 psig or to any other suitable pressure, or it can be vented to the surrounding pressure. Pinch valves 60*g* and 60*c* can be opened and fluid can flow out of heater bag 20, through tube 38, through a sealing Y connection 33*b*, through tube 28, through Y connection 35, and into patient line 34. Because gravity propels the fluid as it flows, air does not enter the patient line. For example, the air can simply remain in the heater bag 20. In some embodiments, a small positive pressure can be applied to facilitate the flow of fluid out of the heater bag 20, or a small negative pressure (e.g., −0.1 psig) can be used to prevent air from entering the patient.

The load cells 75 can measure the change in weight of the heater bag 20 and provide continuous feedback to the controller. The fluid flow rate typically will be between about 125 and 250 ml/min and will generally not slow down unless the patient line 34 is restricted. Pinch valves 60*g* and 60*c* can close when the volume delivered reaches the programmed fill volume. The volume delivered, as measured by the load cells can be recorded in a computer-readable medium.

At block 1414, the volume of fluid in the heater bag, and thus the volume of fluid delivered to the patient, can be determined. The vacuum in containment chamber 6 will be set to a first value (e.g., increased to about −0.5 psig) and the vacuum in the reference chamber 90 can be set to a second value (e.g., about −7 psig). After the two pressures are recorded, the two chambers are connected and the pressure within can be allowed to substantially equalize. The new pressure reading(s) are recorded and used along with the previous pressure readings and the previously calculated post drain/pre-fill containment chamber air volume to calculate the volume of fluid that was delivered to the patient. If the fluid volume as measured by the load cells differs by more than a threshold value (e.g., 10%) from that calculated using the pressure-based system, an alarm will be posted. The calculated post fill air volume of containment chamber 6 can be recorded.

The fluid can be left in the peritoneum of the patient for a time known as the dwell period. At block 1416, during the dwell period, the vacuum in containment chamber 6 can be set to about −0.1 psig, or to any other suitable pressure (e.g., at least about −0.05 and/or less than or equal to about −0.2), or vented to atmospheric pressure, and pinch valve 60*a* can be opened. Gravity can cause the interim drain bag 22 to empty through line 39, through sealing Y connection 33, and into and through drain line 36. The load cells 75 can measure the change in weight of interim drain bag 22 and provide continuous feedback to the controller. The fluid flow rate typically will be between about 125 and about 250 ml/min and will generally not slow down unless the interim drain bag 22 is empty. Pinch valve 60*a* can close when the flow rates stops and the transfer ended if the volume moved is within a threshold value (e.g., 100 ml) of the volume previously drained from the patient. The volume that was transferred from the drain bag 22, as measured by the load cells, can be recorded.

At block 1418, the volume of fluid drained from the drain bag 22 is determined using the pressure system. The pressure in containment chamber 6 can be set to a first value (e.g., about −0.5 psig) and the pressure in the reference chamber can be set to a second value (e.g., about −7 psig). After the two pressures are recorded, the two chambers can be connected and the pressure within can be allowed to substantially equalize. The new pressure readings can be recorded and used along with the previous pressure readings and the previously calculated post fill containment chamber air volume to calculate the volume of fluid that was transferred out of the drain bag 22. If the fluid volume as measured by the load cells differs by more than a threshold value (e.g., 10%) from that calculated using Boyle's Law, an alarm will be posted. The calculated post drain transfer air volume of containment chamber 6 can be recorded.

If the heater bag needs to be replenished prior to the next fill, fluid can be transferred into the heater bag at block 1420. The containment chamber can be evacuated to about −1.5 psig, or to any other suitable value. Pinch valves 60*d* or 60*e* are opened as appropriate and fluid flows from the supply or last bag through lines 31 or 32, through Y connection 37, through tube 27, through sealing Y connection 33, through line 38, and into heater bag 20. Load cells 75 measure the change in weight of the heater bag 20 and provide continuous feedback to the controller. The fluid flow rate typically will initially be between about 125 ml/min and 250 ml/min, or can be less than or equal to about 200 ml/min. The flow rate may start to slow down if the reservoir (e.g., supply bag) empties of fluid. In some embodiments, gravity can be used to transfer the fluid into the heater bag 20. The pressure in containment chamber 6 can be allowed to reduce (e.g., to a value that is at least about −0.5 psig and/or less than or equal to about −1.2 psig, or to any other suitable value) towards the end of the replenish phase if flow slows substantially.

When the replenish phase ends, pinch valve 60*d* or 60*e* can close and the volume of fluid replenished, as measured by the load cells, is recorded. At block 1422, the system can determine the volume of fluid in the heater bag 20 using the pressure system. The pressure in containment chamber 6 can be set to a first value (e.g., about −0.5 psig) and the pressure in the reference chamber 90 can be set to a second value (e.g., about −7 psig). After the two pressures are recorded, the two chambers can be connected and the pressure within can be allowed to substantially equalize. The new pressure reading(s) can be recorded and used along with the previous pressure readings and the previously calculated pre-replenish containment chamber air volume to calculate the volume of fluid that was drawn in to the containment chamber 6. If the fluid volume as measured by the load cells differs by more than a threshold value (e.g., about 10%) from that calculated using the pressure-based system, an alarm can be posted. The system can then return to block 1406 and repeat the cycle if needed.

Many variations to the method 1400 are possible. For example, blocks 1420 and 1422 may be omitted if the heater bag 20 contains enough fluid for the next patient fill stage. Also, block 1408 can be an optional feature, not present in all embodiments. The order of certain described events may be changed. For example, the heater bag 20 could be replenished at blocks 1420 and 1422 before the drain bag 22 is drained at blocks 1416 and 1418 if space permits. The treatment can begin with a drain stage, as described above, in order to drain fluid that was left in the patient after the final fill stage of the previous treatment session. The treatment session can have a fill stage (near the end of the treatment) that is not drained, so that the fluid (e.g., high density dextrose solution) is left in the patient during the time between treatments (e.g., which can be performed daily). In some cases, the treatment session can have a fill stage before the first drain stage, for example, if the patient did not receive an undrained fill stage at a previous treatment. In some cases, the treatment session can begin with a drain stage even if there was no undrained fill stage at a previous treatment (which may result in a low volume initial drain), thereby ensuring that the patient has been cleared before the first fill to reduce the risk of overfilling a patient. Other variations are possible.

In some embodiments, the load cells and/or the pressure-based measurement system are able to determine when the interim drain bag 22 and the heater bag 20 contain fluid. If fluid does not flow from the bags when they contain fluid as expected, an alarm can be posted. If the flow rate unexpectedly drops or stops, an alarm can be posted.

The APD cycler 10 can include a controller configured to controller the APD process. The controller can control the pinch valves 60, the vacuum pump 96, the valves 94 and 99, the heating elements, the alarms, etc. If fluid flow slows or stop during a drain, an alarm, such as a low level, continuously sounding audible alarm can be posted for a time (e.g., at least about 1 second and/or less than or equal to about 10 seconds, or any other suitable time) so that the patient can roll over or otherwise change position. The system can automatically resume the drain for an additional time (e.g., at least about 1 minute and/or less than about 10 minutes) during which time the condition that caused the alarm may be addressed by the user. If the fluid flow remains slow or stopped after the 5 minute delay, a slightly higher level, continuously sounding audible alarm can be posted for a suitable time (e.g., at least about 1 second and/or less than or equal to about 10 seconds, or any other suitable time) so that the patient can roll over or otherwise change position. The system will automatically resume the drain for an additional time (e.g., at least about 1 minute and/or less than about 10 minutes) during which time the condition that caused the alarm may be addressed by the user. If the fluid flow remains slow or stopped after the 5 minute delay, an even higher level, continuously sounding audible alarm can be posted, and can continue until the STOP button is pressed to silence the alarm. The system can automatically resume drain after the STOP button is pushed and can continue without posting an additional alarm for a time (e.g., at least about 1 minute and/or less than about 10 minutes) during which time the condition that caused the alarm may be addressed. Many variations are possible. A beeping alarm may be used. In some cases, a continuous alarm, instead of a beeping alarm, is used as it can be detected by devices used by hearing-impaired individuals to alert them when their phone is ringing or the door bell is sounding. In some cases, the beeping alarms would be ignored by these devices as are doors closing, cars backfiring, etc. In some embodiments, the alarms can sound for 3 seconds, and the system can delay 5 minutes between alarms, although other times may be used, as described above.

In some embodiments, the audible alarm can be suppressed by plugging a suppression device into the parallel output device port. The suppression device can signal a parent, or caregiver (e.g., via a pager or text message or email or other notification). The suppression device can also signal a light signaling device, a bed shaker, or a vibrating pager in the event the patient is hearing-impaired. The suppression device could be incorporated into the cycler itself and turned ON or OFF using the operator interface, or it may be an external device.

The APD cycler 10 can post an alarm when less fluid than expected is drained from the patient to the drain bag 22, possibly indicating a kink or other obstruction in the line (e.g., if the patient rolls onto the line while sleeping). In some embodiments, the system will not post the alarm if close to the full expected amount of fluid was drained. The amount of fluid that failed to drain can be recorded and the volume of fluid to be delivered in later fill stages may be reduced to reduce the risk of overfilling the patient. For example, if several drain stages end prematurely without fully draining the patient's peritoneum and if the full fill volumes are delivered to the patient, the residual fluid left by each incomplete drain can add up resulting in overfilling and discomfort and potential injury to the patient. This may be the case for a system that sets the patient volume to zero for each cycle.

Thus, in some embodiments, the APD cycler 10 can track the volume of fluid in the patient across multiple fill and drain cycles and does not set the patient volume to zero, unless the measured drained volume exceeded the expected drain volume (e.g., volume delivered at the last fill stage, plus expected ultrafiltration (UF) from the patient, plus residual volume left from previous cycles). In some embodiments, the system may also set the patient volume to zero after the initial drain, regardless the measured drain volume. In some embodiments, an expected drain volume can be calculated using fill information from the previous treatment session and the patient volume is automatically set to zero after the initial drain. In some embodiments, the user can input an expected UF value that indicates how much extra fluid is expected to be removed from the patient's body at each drain stage (in excess of the infused fluid from the fill stage).

The system can be configured to determine whether to post an alarm when a drain stops before the expected amount of fluid is drained. In some embodiments, the system can post an alarm if less than a threshold amount of fluid was successfully drained, but if the amount of drained fluid is deemed generally close to the full expected drain value, no alarm is posted and the treatment continues. The threshold amount can be calculated as a percentage (e.g., at least about 75% and/or less than or equal to about 95%, or about 85%) of the full expected patient volume at the start of the drain (e.g., the volume of fluid delivered at the previous fill stage plus any residual fluid remaining from previous cycles), or of the full expected drain volume (e.g., the volume of fluid delivered at the previous fill stage plus any residual fluid remaining from previous cycles plus the expected UF volume).

Table 4 contains a comparison between two systems when consecutive incomplete drains occur during a therapy. In the first example show, the system is configured to continue treatment instead of posting an "incomplete drain" alarm if about 85% of the previously filled fluid was drained, regardless of whether residual fluid remains in the patient from previous cycles. In the second example shown, the system is configured to continue treatment instead of posting an "incomplete drain" alarm if about 85% of the current expected patient volume is successfully drained.

TABLE 4

| Phase | | First Example | | Second Example | |
|---|---|---|---|---|---|
| | | Per Cycler | Actual | Per Cycler | Actual |
| Initial Drain | Start | 2000 | 2000 | 2000 | 2000 |
| | End | 0 | 0 | 0 | 0 |
| Fill 1 | Start | 0 | 0 | 0 | 0 |
| | End | 3000 | 3000 | 3000 | 3000 |
| Dwell 1 | Start | 3000 | 3000 | 3000 | 3000 |
| | End | 3000 | 3300 (110%) | 3300 | 3300 (110%) |
| Drain 1 | Start | 3000 | 3300 | 3300 | 3300 |
| Ends @85% | End | 450 | 750 | 495 | 495 |
| Fill 2 | Start | 0 | 750 | 495 | 495 |
| | End | 3000 | 3750 | 3495 | 3495 |
| Dwell 2 | Start | 3000 | 3750 | 3495 | 3495 |
| | End | 3000 | 4050 (135%) | 3795 | 3795 (127%) |
| Drain 2 | Start | 3000 | 4050 | 3795 | 3795 |
| Ends @85% | End | 450 | 1500 | 569 | 569 |
| Fill 3 | Start | 0 | 1500 | 569 | 569 |
| | End | 3000 | 4500 | 3569 | 3569 |
| Dwell 3 | Start | 3000 | 4500 | 3569 | 3569 |
| | End | 3000 | 4800 (160%) | 3869 | 3869 (129%) |
| Drain 3 | Start | 3000 | 4800 | 3869 | 3869 |
| Ends @85% | End | 450 | 2250 | 580 | 580 |
| Fill 4 | Start | 0 | 2250 | 580 | 580 |
| | End | 3000 | 5250 | 3580 | 3580 |
| Dwell 4 | Start | 3000 | 5550 | 3580 | 3580 |
| | End | 3000 | 5950 (185%) | 3880 | 3880 (129%) |

(values in milliliters)

As shown in Table 4, in the first example, the patient can be overfilled by about 10% after one incomplete drain, by about 35% after two incomplete drains, by about 60% after three incomplete drains, and by about 85% after four incomplete drains. In the second example, the patient is overfilled by about 10% after one incomplete drain, by about 27% after two incomplete drains, by about 29% after three incomplete drains, and again by about 29% after four incomplete drains. In the second example, the system tracks of the expected patient volume and limits the magnitude of any potential overfills.

Figure 15:
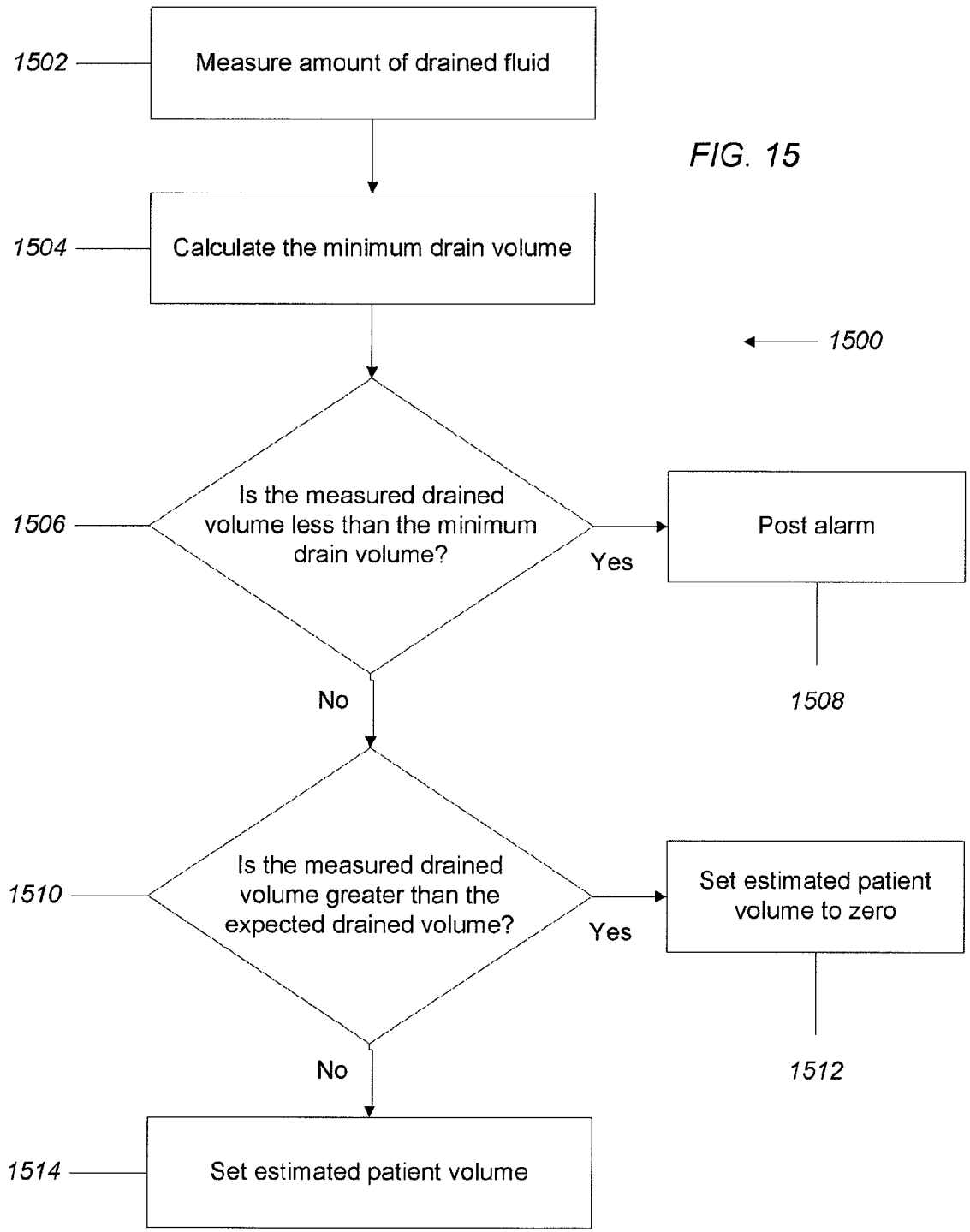
FIG. 15 is a flowchart that shows an example embodiment of a method of handling a drain stage in an automated peritoneal dialysis treatment.

FIG. 15 is a flowchart that illustrates an example embodiment of a method 1500 for handling a drain stage. If the system receives an indicator that the drain may be completed (e.g., the flow rate stops or drops below a threshold "slow flow" or "no flow" level), the system can perform the method 1500. At block 1502, the amount of fluid drained from the patient is measured. The measurement can be made by the load cells 75, other weight scale, and/or by the pressure-based system described herein. At block 1504, the minimum drain volume can be calculated. For example, the minimum drain volume can be the expected drain volume (e.g., the volume of fluid delivered at the previous fill stage plus any residual fluid remaining from previous cycles plus the expected UF volume) multiplied by a minimum drain percentage (e.g., about 85%). At block 1506, the system can determine whether the measured drain volume is less than the minimum threshold drain volume. If the measured drain volume is less than the minimum threshold drain volume, the process 1500 can proceed to block 1508 and post an "incomplete drain" alarm. The alarm can be designed to awaken the patient so that the patient can shift position to unblock the drain line or take other appropriate action. If the measured drain volume is not less than the minimum threshold drain volume, the process 1500 proceeds to block 1510, and updates the expected patient volume. If the measured volume of drained fluid exceeds the expected drain amount, the estimated patient volume can be set to zero, at block 1512. If the measured drained fluid is less than the expected drain volume, the system can add the difference to the estimated patient volume, at block 1514, which may be used for future calculations.

The overfill limit can be calculated from the prescribed fill volume, the minimum drain percentage and the expected per cycle UF as follows:

$$\text{Fill Limit} = (\text{Prescribed Fill Volume} + \text{Per Cycle UF}) / \text{Min Drain \%}$$

In the embodiment shown in the second example of Table 1, the fill limit is calculated to be (3000+300)/0.85=3882 ml.

Conversely, the minimum drain % can be calculated from a selected fill limit, the prescribed fill volume and the per cycle UF as follows:

$$\text{Min Drain \%} = (\text{Prescribed Fill Volume} + \text{Per Cycle UF}) / \text{Fill Limit}$$

In the embodiment shown in the second example of Table 1, the min drain percentage is calculated to be (3000+300)/3882=0.85=85%. If the user wishes to limit the amount of potential overfilling to a different number (e.g., 3500 ml), the appropriate drain percentage can be calculated (e.g., (3000+300)/3500=0.94=94%). The user can input the desired over fill limit, the expected UF, and the per cycle fill volume, and the system can select an appropriate minimum drain percentage. If the user selects a low maximum fill limit, then the system will be more sensitive to incomplete drains (e.g., posting an alarm if only a small amount of fluid fails to drain), and if the use selects a relatively high maximum fill limit, then the system will only post an alarm is a relatively large amount of fluid fails to drain.

In some embodiments, bypassing a minimum drain volume alarm can cause the system to deliver less fluid in later fill stages, thereby further preventing patient overfilling. In some embodiments, an additional cycle can be added to the treatment session to compensate for the amount of fluid that is reduced from the fill stages. The new fill volume can be determined by dividing the remaining therapy volume, excluding last fill volume, by the number of remaining cycles (including the newly added cycle). If needed, multiple additional cycles can be added, for example, if the predicted patient volume at the end of the dwell would still exceed a desired volume after one additional cycle is added. This method of reducing the later fill volumes can result in all of the available therapy volume being used while preventing the patient from being filled to a volume that is greater than a desired limit. The system can add an additional infusion cycle to a treatment session schedule. The system can determine an amount of infusion fluid remaining to be infused during the dialysis treatment, and the system can calculate an adjusted infusion volume by dividing the amount of infusion fluid remaining by the number of scheduled infusion cycles. The system can infuse the adjusted infusion volume of dialysis solution into the patient.

In some embodiments, the system can record the ultrafiltration values for each therapy and calculate an average UF for the patient. If the programmed expected UF varies by more than a threshold amount (e.g., about 50%) from this average value the system can notify the user that the inputted expected UF may be inappropriate. The system can display the average UF value to the patient and ask the patient to confirm the original value or input a new expected UF value. If a patient uses different Dextrose solutions, the UF can be recorded and an average can be calculated for multiple (e.g., 2 or 3 or more) different Dextrose concentrations. The UF target for a therapy can then be programmable for each of the different Dextrose concentrations. In some embodiments, the system can use the average UF value if no expected UF value is provided by the user.

The APD cycler 10 can operate on 100-250V 50/60 Hz AC. A universal voltage power supply can be used. In some cases the heating elements can be powered by a dedicated power supply. A single heating element may be used, or multiple heading elements (e.g., 2 or 3 or more) can be used. When the system is powered "ON" the heating elements can be configured in series. A comparator circuit can check the voltage drop across a circuit to determine whether the input power was 90-132 volts or 180-275 volts or some other value. If the input power is 180-275VAC, the heaters can continue to operate in series. If the power is 90-132VAC the heaters can be switched to operate in parallel. The system can retain the heater configuration after momentary power glitches.

The system can use pulse width modulation (PWM) techniques to further refine the power output by the heater elements. For example, a 400 watt heater could be powered "ON" for 50 msec and "OFF" for 50 msec to produce an output of 200 watts. This technique could also be used in lieu of the series/parallel configuring of the heater elements to allow the system to operate throughout the 100-250 V 50/60 Hz AC range.

The heater elements can be isolated from the heater tray by at least two layers of electrical insulators rather than one layer of insulation so that a "pin hole" in one layer would not compromise the effectiveness of the insulation and compromise patient safety.

Some aspects of the systems and methods described herein can be implemented using, for example, computer software, hardware, firmware, or any combination of computer software, hardware, and firmware. Computer software can include computer executable code stored in computer readable medium (e.g., non-transitory computer readable medium) that, when executed, causes one or more computing devices to perform the functions described herein. In some embodiments, computer-executable code is executed by one or more general purpose computers. It will be appreciated, in light of this disclosure, that any feature or function that can be implemented using software to be executed on one or more general purpose computers can also be implemented using a different combination of hardware, software, and/or firmware. For example, such a feature of function can be implemented completely in hardware using a combination of integrated circuits. Alternatively or additionally, such a feature or function can be implemented completely or partially using one or more specialized computers designed to perform the particular functions described herein rather than by general purpose computers.

Multiple distributed computing devices can be substituted for any computing device described herein. In such distributed embodiments, the functions of the one computing device are distributed (e.g., over a network) such that some functions are performed on each of the distributed computing devices.

Some features of this disclosure may be described with reference to equations, algorithms, and/or flowcharts. These methods may be implemented using computer program instructions executable on one or more computing devices, using one or more computer processors. These methods may also be implemented as computer software either separately from, or as a component of, an apparatus or system. In this regard, each equation, algorithm, or block or step of a flowchart, and combinations thereof, may be implemented by hardware, firmware, and/or software including computer program instructions embodied in computer-readable medium.

As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or by combinations of special purpose hardware and computer-readable program code logic means.

Any features of the embodiments shown and/or described in the figures that have not been expressly described in this text, such as distances, proportions of components, etc. are also intended to form part of this disclosure. Additionally, although these inventions have been disclosed in the context of various embodiments, features, aspects, and examples, it will be understood by those skilled in the art that the present inventions extend beyond the specifically disclosed embodiments to other alternative embodiments and/or uses of the inventions and obvious modifications and equivalents thereof. Accordingly, it should be understood that various features and aspects of the disclosed embodiments can be combined with, or substituted for, one another in order to perform varying modes of the disclosed inventions. The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart blocks. It will be understood that in many cases, certain steps may be combined together such that multiple steps shown in the flowcharts can be performed as a single step. Also, certain steps can be broken in to additional sub-steps to be performed separately. In many instances, the order of the steps can be rearranged and certain steps may be omitted entirely. Also, the methods described herein are to be understood to be open-ended, such that additional steps to those shown and described herein can also be performed. Thus, it is intended that the scope of the present inventions disclosed herein should not be limited by the particular disclosed embodiments described herein.

The following is claimed:

1. A method of performing a dialysis treatment comprising:
   infusing an infusion volume of dialysis solution into a patient;
   draining fluid from a patient;
   identifying an indicator that the draining may be complete;
   measuring the volume of drained fluid;
   calculating a minimum drain volume, wherein the minimum drain volume is a predetermined percentage of an expected drain volume, wherein the expected drain volume comprises the infusion volume and an estimated residual patient volume; and
   determining, using one or more computing devices, if the measured volume of drained fluid is less than the minimum drain volume.

2. The method of claim 1, further comprising posting an alarm if the measured volume of drained fluid is less than the minimum drain volume.

3. The method of claim 1, further comprising continuing the dialysis treatment if the measured volume of drained fluid is not less than the minimum drain volume.

4. The method of claim 3, further comprising updating the estimated residual patient volume to be the difference between the expected drain volume and the measured volume of drained fluid.

5. The method of claim 4, further comprising performing a subsequent infusion stage and a subsequent drain stage, and using the updated estimated residual patient volume to calculate the minimum drain volume for the subsequent drain stage.

6. The method of claim 3, further comprising reducing a volume of a subsequent infusion stage if the measured volume of drained fluid is less than the expected drain volume.

7. The method of claim 6, further comprising:
   adding an additional infusion cycle to a treatment session schedule;
   determining an amount of infusion fluid remaining to be infused during the dialysis treatment;
   calculating an adjusted infusion volume by dividing the amount of infusion fluid remaining by a number of scheduled infusion cycles; and
   infusing the adjusted infusion volume of dialysis solution to the patient.

8. The method of claim 1, wherein the expected drain volume further comprises an expected ultrafiltration volume.

9. The method of claim 1, further comprising:
   infusing a second infusion volume of dialysis solution into the patient;
   draining fluid from the patient a second time;
   measuring a second volume of drained fluid;
   calculating a second minimum drain volume larger than the minimum drain volume,
   wherein the second minimum drain volume is the predetermined percentage of a second expected drain volume, wherein the second expected drain volume comprises the second infusion volume and a second estimated residual patient volume, wherein the second estimated residual patient volume is based at least in part on the difference between the expected drain volume and the measured volume of drained fluid; and
   determining if the second measured volume of drained fluid is less than the second minimum drain volume.

10. The method of claim 1, wherein the predetermined percentage is determined using a formula that comprises $A=(B+C)/(D)$, wherein:
    A comprises the predetermined percentage;
    B comprises the infusion volume;
    C comprises an expected per cycle ultrafiltration; and
    D comprises a fill limit.

11. A dialysis system comprising:
    an infusion system configured to infuse an infusion volume of dialysis solution into a patient;
    a drainage system configured to drain fluid from the patient into a drain container;
    a controller configured to:
      identify an indicator that a drain may be complete;
      determine a drain volume of the fluid in the drain container;
      determine a minimum drain volume, wherein the minimum drain volume is a predetermined percentage of an expected drain volume, wherein the expected drain volume comprises the infusion volume and an estimated residual patient volume; and
      determine if the drain volume is less than the minimum drain volume.

12. The dialysis system of claim 11, wherein the controller is configured to post an alarm if the drain volume is less than the minimum drain volume.

13. The dialysis system of claim 11, wherein the controller is configured to continue dialysis treatment if the drain volume is not less than the minimum drain volume.

14. The dialysis system of claim 13, wherein the controller is configured to update the estimated residual patient volume to be the difference between the expected drain volume and the drain volume.

15. The dialysis system of claim 14, wherein the controller is configured to perform a subsequent infusion stage and a subsequent drain stage, and to use the updated estimated residual patient volume to calculate an updated minimum drain volume for the subsequent drain stage.

16. The dialysis system of claim 13, wherein the controller is configured to reduce a volume of a subsequent infusion stage if the drain volume is less than the expected drain volume.

17. The dialysis system of claim 16, where in the controller is configured to:
    add an additional infusion cycle to a treatment session schedule;
    determine an amount of infusion fluid remaining to be infused during a dialysis treatment; and
    determine an adjusted infusion volume by dividing the amount of infusion fluid remaining by the number of scheduled infusion cycles.

18. The dialysis system of claim 11, wherein the expected drain volume further comprises an expected ultrafiltration volume.

19. The dialysis system of claim 11, wherein:
    the infusion system is configured to infuse a second infusion volume of dialysis solution into the patient;
    the drainage system is configured to drain fluid from the patient into the drain container a second time; and
    the controller is configured to:
        determine a second drain volume of the fluid drained into the drain container a second time;
        determine a second minimum drain volume larger than the minimum drain volume, wherein the second minimum drain volume is the predetermined percentage of a second expected drain volume, wherein the second expected drain volume comprises the second infusion volume and a second estimated residual patient volume, wherein the second estimated residual patient volume is based at least in part on the difference between the expected drain volume and the drain volume; and
    determining if the second drain volume is less than the second minimum drain volume.

20. The dialysis system of claim 11, wherein the predetermined percentage is determined using a formula that comprises $A=(B+C)/(D)$, wherein:
    A comprises the predetermined percentage;
    B comprises the infusion volume;
    C comprises an expected per cycle ultrafiltration; and
    D comprises a fill limit.

* * * * *